(12) United States Patent
Wikfors

(10) Patent No.: US 10,478,749 B2
(45) Date of Patent: Nov. 19, 2019

(54) APPARATUS AND METHOD FOR INTRODUCING A SAMPLE INTO A SEPARATION UNIT OF A CHROMATOGRAPHY SYSTEM

(71) Applicant: Agilent Technologies, Inc., Santa Clara, CA (US)

(72) Inventor: Edwin E. Wikfors, Landenberg, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 172 days.

(21) Appl. No.: 15/314,717

(22) PCT Filed: May 29, 2014

(86) PCT No.: PCT/US2014/040073
§ 371 (c)(1),
(2) Date: Nov. 29, 2016

(87) PCT Pub. No.: WO2015/183290
PCT Pub. Date: Dec. 3, 2015

(65) Prior Publication Data
US 2017/0100682 A1    Apr. 13, 2017

(51) Int. Cl.
*G01N 30/20* (2006.01)
*G01N 30/34* (2006.01)
(Continued)

(52) U.S. Cl.
CPC ............ *B01D 15/14* (2013.01); *B01D 15/18* (2013.01); *B01D 15/325* (2013.01); *B01D 15/40* (2013.01);
(Continued)

(58) Field of Classification Search
CPC ........ G01G 21/24; B01D 15/14; B01D 15/18; B01D 15/325; B01D 15/40;
(Continued)

(56) References Cited

U.S. PATENT DOCUMENTS

| 4,374,656 A | * | 2/1983 | Schrenker | B01D 19/00 96/194 |
| 2002/0011437 A1 | * | 1/2002 | Kaito | G01N 30/34 210/198.2 |

(Continued)

FOREIGN PATENT DOCUMENTS

| EP | 0385026 A2 | 9/1990 |
| WO | 2014034259 A1 | 3/2014 |
| WO | 2014085003 A2 | 6/2014 |

OTHER PUBLICATIONS

Extended European Search Report issued in counterpart EP Application No. 14892885.6 dated Feb. 19, 2018 (nine (9) pages).
(Continued)

*Primary Examiner* — Natalie Huls
*Assistant Examiner* — Monica S Young

(57) ABSTRACT

An apparatus introduces a sample into a separation unit of a chromatography system with a mobile phase, including first and second mobile phase components. The apparatus includes first and second pump systems, and an injection unit. The first pump system provides the first mobile phase component, first and second portions of the first mobile phase component flowing through first and second branches, respectively. The second pump system provides the second mobile phase component, a first portion of the second mobile phase component flowing through a third branch. The injection unit receives a combined stream of the first portions of the first and second mobile phase components provided via the first and third branches, respectively, and injects the sample into the combined stream to form a
(Continued)

sample-containing stream, which is subsequently combined with the second portion of the first mobile phase component to form a diluted sample-containing stream.

15 Claims, 13 Drawing Sheets

(51) Int. Cl.
*G01N 30/16* (2006.01)
*G01N 30/32* (2006.01)
*G01N 30/38* (2006.01)
*G01N 30/46* (2006.01)
*G01N 30/02* (2006.01)
*B01D 15/14* (2006.01)
*B01D 15/40* (2006.01)
*B01D 15/32* (2006.01)
*B01D 15/18* (2006.01)

(52) U.S. Cl.
CPC ............ *G01N 30/02* (2013.01); *G01N 30/16* (2013.01); *G01N 30/20* (2013.01); *G01N 30/32* (2013.01); *G01N 30/34* (2013.01); *G01N 30/38* (2013.01); *B01D 15/1878* (2013.01); *G01N 30/463* (2013.01); *G01N 30/465* (2013.01); *G01N 2030/324* (2013.01); *G01N 2030/342* (2013.01)

(58) Field of Classification Search
CPC .... B01D 15/1878; G01N 30/16; G01N 30/20; G01N 30/32; G01N 30/34; G01N 30/38; G01N 30/463; G01N 30/465; G01N 2030/324; G01N 2030/342

USPC .......................................................... 177/255
See application file for complete search history.

(56) References Cited

U.S. PATENT DOCUMENTS

| | | | |
|---|---|---|---|
| 2003/0026704 A1* | 2/2003 | Berger | G01N 30/32 417/53 |
| 2003/0034307 A1 | 2/2003 | Berger et al. | |
| 2006/0219633 A1 | 10/2006 | Horsman et al. | |
| 2007/0144977 A1* | 6/2007 | Kitagawa | G01N 30/34 210/787 |
| 2008/0264848 A1 | 10/2008 | Wheat et al. | |
| 2008/0302423 A1 | 12/2008 | Gerhardt et al. | |
| 2009/0165873 A1 | 7/2009 | Chordia et al. | |
| 2009/0205409 A1* | 8/2009 | Ciavarini | G01N 30/34 73/61.56 |
| 2010/0107742 A1 | 5/2010 | Liu et al. | |
| 2012/0285558 A1* | 11/2012 | Witt | F04B 13/00 137/544 |
| 2013/0340508 A1* | 12/2013 | Osaka | G01N 30/468 73/61.53 |
| 2014/0061133 A1* | 3/2014 | Herman | G01N 30/20 210/659 |
| 2015/0316516 A1* | 11/2015 | Albrecht, Jr. | G01N 30/20 73/61.56 |

OTHER PUBLICATIONS

International Search Report from related International Application No. PCT/US2014/040073.

* cited by examiner

APPARATUS AND METHOD FOR INTRODUCING A SAMPLE INTO A SEPARATION UNIT OF A CHROMATOGRAPHY SYSTEM

RELATED APPLICATIONS

This application is the national stage under 35 U.S.C. § 371 of International Application No. PCT/US2014/040073, filed May 29, 2014, titled "APPARATUS AND METHOD FOR INTRODUCING A SAMPLE INTO A SEPARATION UNIT OF A CHROMATOGRAPHY SYSTEM," the content of which is incorporated herein by reference in its entirety.

BACKGROUND

The purpose of a chromatography system is to separate compounds of a sample with a chromatographic column. For example, a sample containing various compounds, dissolved in a solvent solution, may be injected into a mobile phase fluid stream with an injection valve, the fluid stream typically comprising one or more solvents. The sample-containing stream flows through the chromatographic column which may retain the compounds from the sample. The compounds from the sample experience a differential retention with the column's stationary phase, e.g., using packing material or sorbent within the chromatographic column, and the relative elution strength of the mobile phase. The separated compounds may then be directed to a detector for detection and analysis, where each of the compounds emerges from the chromatographic column at a different time corresponding to the respective differential retention of that compound within the chromatographic column. Detection over time results in "peaks" respectively corresponding to the components of the sample, where the magnitude of each peak correlates to the amount of the corresponding component in the sample. In preparative chromatography systems, the separated sample constituents may be collected by various fraction collection devices.

Typically, the sample-containing stream is a mixture of solvents provided by corresponding pump systems. The solvents include at least a strong solvent and a weak solvent referring to the solvents' relative elution strength in relation to each other and to the stationary phase being used. The strong solvent favors a partitioning of the sample components into the mobile phase, thus lessening retention, or providing faster transiting through the chromatographic column. The weak solvent favors partitioning of the sample components on the column's stationary phase thus increasing retention, and may serve to moderate the effects of the strong solvent. Attempts are made to balance the mobile phase composition or ratio between the strong and weak solvents in order to provide an acceptable compromise between speed of the chromatography operation and quality of the analytical results. However, when the sample is injected, the sample's own solvent adds to the partitioning effects of the mobile phase strong solvent. These partitioning effects favor residence in the mobile phase relative to the stationary phase and result in the sample smearing (not focusing) across a large portion on the column. This initial smearing caused by sample solvent effects represents a loss of resolution and broad signals seen with the detector. These degrading effects are even more pronounced in the large volume injections of preparative chromatography, and use in multi-dimensional chromatography where the sample solvent may represent a mobile phase segment cut from a separate chromatographic stream (one dimension) for injection into a second chromatographic stream (second dimension).

Two general types of chromatography systems are supercritical fluid chromatography (SFC) and high performance liquid chromatography (HPLC). SFC with packed columns typically uses an organic solvent, such as methanol, as the strong solvent and highly compressed dense carbon dioxide ($CO_2$) as the weak solvent, SFC, the strong solvent may also be referred to as a modifier solvent. HPLC is generally practiced with two separation classes, normal phase and reverse phase. Normal phase HPLC may use a relatively polar solvent, such as isopropanol, as the strong solvent and a relatively non-polar solvent, such as hexane, as the weak solvent. Reverse phase HPLC may use an organic solvent, such as acetonitrile, as the strong solvent and water as the weak solvent. In other configurations of reverse phase HPLC, the organic strong solvent may also be referred to as a hydrophobic solvent or anon-polar solvent, and the aqueous weak solvent may be referred to as a hydrophilic solvent or a polar solvent.

An example of conventional SFC is provided by U.S. Pat. No. 6,576,125 to Berger et al. (issued Jun. 10, 2003), and an example of conventional HPLC is provided by U.S. Pat. No. 6,790,361 to Wheat et al. (issued Sep. 14, 2004), both of which are hereby incorporated by reference in their entireties. These patents are generally directed to standard injection techniques, in which the sample is injected into the full, combined mobile phase, and further include presenting the sample to the column in a diluted form at the same solvent composition as the mobile phase. However, such diluted sample loading is at the expense of increased loading times. Further, these techniques do not address samples dissolved in a sample solvent of greater solvent strength than the mobile phase strong solvent into which they are injected.

It is desirable to not only balance the mobile phase composition or ratio between the strong and weak solvents in the sample-containing stream entering the chromatographic column to optimize the speed and results of the chromatography operation, but additionally provide adjustability to the control relating to the dilution of the sample solvent with either or both components of the mobile phase and to the loading time of the sample as it is presented to the column. Such control would allow generally increased sample loading amounts and/or increased resolution in the separation of sample compounds. Further, such control would enable compensating for changes in solvent strength during the injection process, for example, when the sample solvents have greater strength than the mobile phase solvent. This requires precise, independent control of each solvent providing the sample-containing stream, both before and after injection of the sample, which is not present in the conventional chromatography systems.

SUMMARY

In a representative embodiment, an apparatus is provided for introducing a sample into a separation unit of a chromatography system with a mobile phase, the mobile phase comprising a first mobile phase component and a second mobile phase component. The apparatus includes first and second pump systems and an injection unit. The first pump system is configured to provide the first mobile phase component, a first portion of the first mobile phase component flowing through a first branch, and a second portion of the first mobile phase component flowing through a second branch. The second pump system is configured to provide the second mobile phase component, a first portion of the second mobile phase component flowing through a third branch, and a second portion of the second mobile phase component flowing through a fourth branch. The injection unit is configured to receive a combined stream, including the first portion of the first mobile phase component provided via the first branch and the first portion of the second mobile phase component provided via the third branch, and to inject the sample into the combined stream to form a sample-containing stream. The sample-containing stream is subsequently combined with the second portion of the first mobile phase component provided via the second branch and the second portion of the second mobile phase component provided via the fourth branch to form a diluted sample-containing stream, which flows to the separation unit of the chromatography system for separating sample constituents.

In another representative embodiment, a method is provided for injecting a sample in a chromatography system with a mobile phase comprising a first mobile phase component and a second mobile phase component. The method includes proportioning the first mobile phase component into corresponding first and second portions of the first mobile phase component; proportioning the second mobile phase component into corresponding first and second portions of the second mobile phase component; combining the first portion of the first mobile phase component and the first portion of the second mobile phase component to form a combined stream; injecting a sample solution into the combined stream to form a sample-containing stream; combining the sample-containing stream with the second portion of the first mobile phase component and the second portion of the second mobile phase component to form a diluted sample-containing stream; and passing the diluted sample-containing stream to a chromatographic column. The method may further include varying the second portion of the first mobile phase component to adjust an amount of dilution of the diluted sample-containing stream.

BRIEF DESCRIPTION OF THE DRAWINGS

The representative embodiments are best understood from the following detailed description when read with the accompanying drawing figures. Wherever applicable and practical, like reference numerals refer to like elements.

DETAILED DESCRIPTION

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that as used in the specification and appended claims, the terms "a", "an" and "the" include both singular and plural referents, unless the context clearly dictates otherwise. Thus, for example, "a device" includes one device and plural devices.

As used in the specification and appended claims, and in addition to their ordinary meanings, the terms "substantial" or "substantially" mean to within acceptable limits or degree. For example, "substantially cancelled" means that one skilled in the art would consider the cancellation to be acceptable. As a further example, "substantially removed" means that one skilled in the an would consider the removal to be acceptable.

As used in the specification and the appended claims and in addition to its ordinary meaning, the term "approximately" means to within an acceptable limit or amount to one having ordinary skill in the art. For example, "approximately the same" means that one of ordinary skill in the art would consider the items being compared to be the same.

Generally, various embodiments of the present invention provide first and second pump systems that provide first (e.g., weak) and second (e.g., strong) solvents in a mobile phase, at an input and an output of an injection unit that injects sample into the solvent mixture. Each of the first and second pump systems may be connected to multiple branches having different restrictions, so that portions of the first solvent flow through corresponding multiple branches in desired proportions, and likewise so that portions of the second solvent flow through corresponding multiple branches in desired proportions. Accordingly, the ratios between the first and second solvents at both the input and output of the injection unit may be precisely determined and controlled. Also, in various embodiments, the amount of restriction in one or more of the branches may be changed and/or selectively applied in order to alter the mixture ratios to improve or optimize the chromatography operation.

Figure 1:
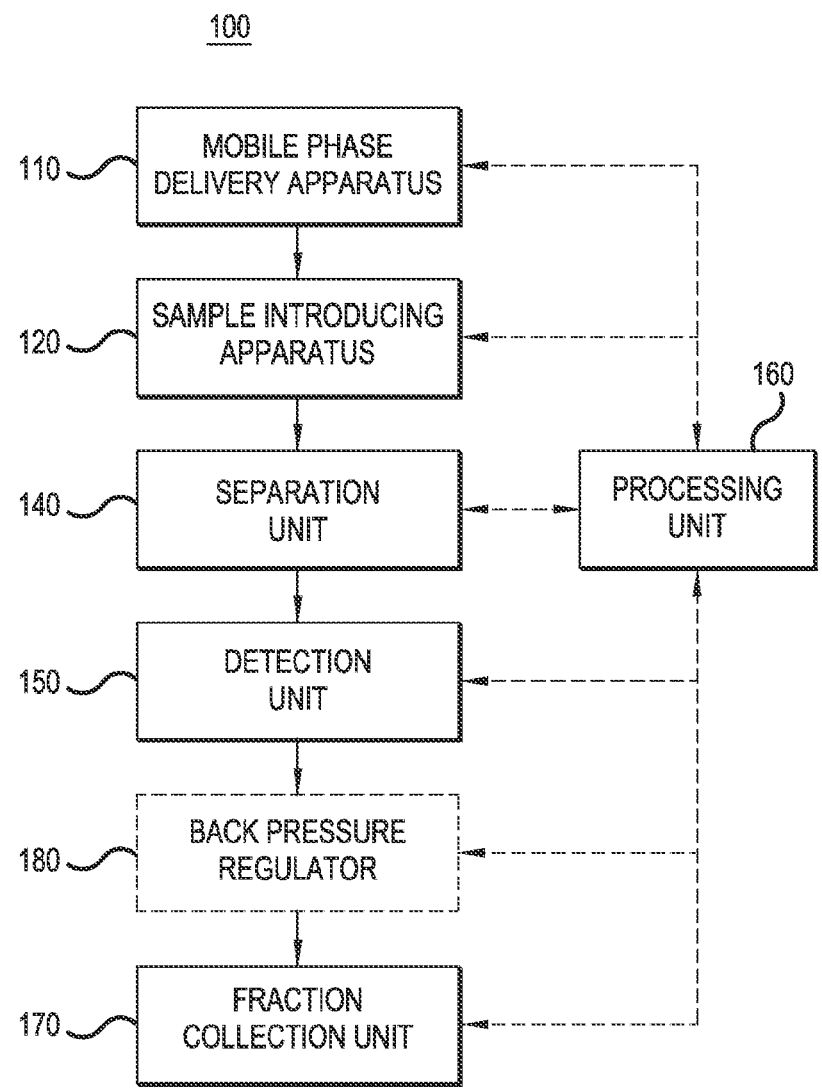
FIG. 1 is a simplified block diagram of a chromatography system, including a mobile phase bridge apparatus, according to a representative embodiment.

FIG. 1 is a simplified block diagram of a chromatography system, including a mobile phase bridge apparatus, according to a representative embodiment.

Referring to FIG. 1, chromatography system 100 includes mobile phase delivery apparatus 110, sample introducing apparatus 120, separation unit 140, detection unit 150 and optionally a fraction collection unit 170. The mobile phase delivery apparatus 110 is configured to receive and deliver at least two fluids from respective reservoirs (not shown). These fluids, in combination, form the chromatographic mobile phase. The sample introducing apparatus 120 is configured to receive mobile phase constituents from mobile phase delivery apparatus 110 in at least two independent paths. The sample introducing apparatus 120 injects sample into the received mobile phase constituents in manners herein described, and provides the sample-containing mobile phase to the separation unit 140. Typically, the fluids delivered from mobile phase delivery apparatus 110 to sample introducing apparatus 120 include a strong solvent and a weak solvent, which are provided in various proportions to affect aspects of chromatography in the separation unit 140.

The separation unit 140 comprises a stationary phase, and is configured to separate compounds of the sample (sample constituents) in the sample-containing solution. The separation unit 140 may be implemented as one or more chromatographic columns, for example. More particularly, as discussed above, the separation unit 140 separates (elutes) the compounds from the sample-containing stream by differential retention of the compounds, e.g., using packing material or sorbent typically applied within the inner walls of the separation unit 140. The compounds are emitted from the separation unit 140 at different times corresponding to the respective differential retentions of compounds within the chromatographic column. A detection unit 150 is provided for detecting separated compounds of the sample fluid. SFC systems may include a back pressure regulator 180 (shown in dashed lines) or similar pressure reducing device positioned after the detection unit 150.

The chromatography system 100 may further include a processing unit 160 connected to one or more of the mobile phase delivery apparatus 110, sample introducing apparatus 120, the separation unit 140, the detection unit 150, back pressure regulator 180, and the fraction collection unit 170 (indicated by dashed lines) for controlling aspects of the chromatography process. For example, the processing unit 160 may control operation of pump systems, branch restrictions (discussed below) and/or mixture ratios in the sample introducing apparatus, as well as monitor various control parameters, such as pressure, flow rates, and the like. The processing unit 160 may also control the amount of sample injected into the mixed solvent. In addition, the processing unit 160 may receive data regarding sample detection (e.g., detected peaks, peak widths, resolution, efficiency, corresponding to compounds separated by the separation unit 140) from the detection unit 150. The received data may be displayed and/or stored for analysis, or used to adjust control elements relating to injection, pumping, or separation, for example.

Generally, the processing unit 160 may be implemented by a computer processor (e.g., of a personal computer (PC) or dedicated workstation), application specific integrated circuits (ASICs), field-programmable gate arrays (FPGAs), or combinations thereof, using software, firmware, hard-wired logic circuits, or combinations thereof. A computer processor, in particular, may be constructed of any combination of hardware, firmware or software architectures, and may include memory (e.g., volatile and/or nonvolatile memo) for storing executable software/firmware executable code that allows it to perform the various functions. In an embodiment, the computer processor may comprise a central processing unit (CPU), for example, executing an operating system.

Figure 2:
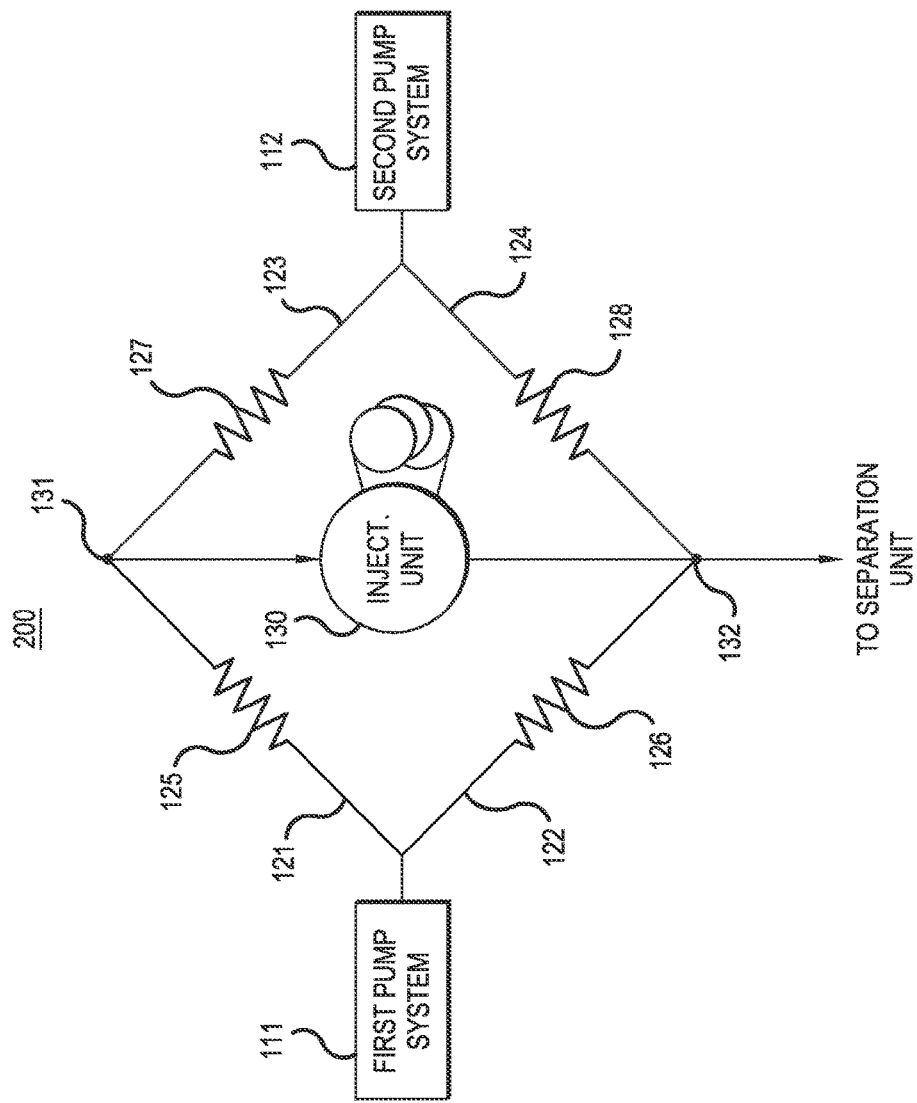
FIG. 2 is a simplified block diagram of a mobile phase bridge apparatus in a chromatography system, according to another representative embodiment.

FIG. 2 is a simplified block diagram of a mobile phase bridge apparatus comprising mobile phase delivery apparatus and sample introducing apparatus in a chromatography system, according to a representative embodiment.

Referring to FIG. 2, the mobile phase bridge apparatus 200 includes first pump system 111 and second pump system 112 for delivering the mobile phase, where each of the first and second pump systems 111 and 112 may include one or more pumps. The pumps represented by at least the first pump system 111 and second pump system 112 comprise the mobile phase delivery apparatus 110. The first and second pump systems 111 and 112 may include multiple piston, positive displacement pumps or other types of pumps capable of delivering a pulseless consistent flow stream, for example.

The first pump system 111 provides first mobile phase components of the mobile phase and the second pump system 112 provides second mobile phase components of the mobile phase, where each of the first and second mobile phase components may be a solvent or mixture of solvents received from corresponding reservoirs (not shown). For purposes of illustration, it may be assumed that the first mobile phase component provided by the first pump system 111 is the weak solvent, and that the second mobile phase component provided by the second pump 112 is the strong solvent, relative to one another, although this may vary without departing from the scope of the present teachings. The general configuration of the first and second pump systems 111 and 112 may be substantially the same for SFC systems and HPLC systems. For example, in an SFC system, the weak solvent provided by the first pump 111 may include compressed carbon dioxide ($CO_2$), and the strong solvent provided by the second pump 112 may include an organic solvent, such as methanol. In an HPLC system, the weak solvent provided by the first pump 111 may include water or hexane, and the strong solvent provided by the second pump 112 may include an organic solvent, such as acetonitrile or isopropanol, for example. The actual nature of strong and weak solvents is determined by the nature of the chromatographic methods (e.g., SFC, normal phase HPLC, reverse phase HPLC, and the like) and are not meant to be limited by these exemplary definitions.

The first pump system 111 is configured to provide the first mobile phase component to a first branch 121 and a second branch 122, such that a first portion of the first mobile phase component flows through the first branch 121 and a second portion of the first mobile phase component flows through the second branch 122. Likewise, the second pump system 112 is configured to provide the second mobile phase component to a third branch 123 and a fourth branch 124, such that a first portion of the second mobile phase component flows through the third branch 123 and a second portion of the second mobile phase component flows through the fourth branch 124.

In the depicted embodiment, the first and third branches 121 and 123 join with one another at input junction 131, connected to the input of an injection unit 130, to provide a combined stream. The combined stream includes a mixture of the first portion of the first mobile phase component from the first pump system 111 and the first portion of the second mobile phase component from the second pump system 112. The injection unit 130 receives the combined stream, and injects sample into the combined steam to create a sample-containing stream, which is output from the injection unit 130 to output junction 132. The second and fourth branches 122 and 124 join with one another and the sample containing stream from injection unit 130 at the output junction 132 to provide a diluted sample-containing stream. While the output junction 132 is illustratively shown as a single intersection of three individual streams, it is understood that in alternative configurations, two of the streams may intersect initially, and later combine with the third stream, without departing from the scope of the present teachings. For example, one of the streams from the second and fourth branches 122 and 124 may individually intersect with the sample containing stream, and the combination of these two streams may subsequently combine with the other one of the streams front the second and fourth branches 122 and 124. The diluted sample-containing stream includes the second portion of the first mobile phase component, the second portion of the second mobile phase component, and the sample-containing stream output by the injection unit 130. The diluted sample-containing stream flows to a separation unit of the chromatography system (e.g., separation unit 140, discussed above) for separating sample constituents.

The sample may be dissolved in an organic solvent, such as methanol or water for example, prior to injection into the combined stream of the mobile phase by the injection unit 130. The injection unit 130 may be implemented as an injector valve, for example, such as a fixed-loop, multi-port injector valve with internal or external sample loops or more involved valving employing means of collecting solutes for reinjection in other chromatographic streams. The sample may be automatically injected into a sample loop, or manually injected using a syringe via a fill port. Different types of injection units 130 may be incorporated for SEC and HPLC, and multi-dimensional chromatography systems, as would be apparent to one of ordinary skill in the art.

The relative amounts of first and second mobile phase components that are mixed at the input and output junctions 131 and 132 may be functions of restrictions in the first through fourth branches 121 to 124, respectively, i.e., restricting the flow of the corresponding first and second mobile phase components. In the depicted embodiment, the first branch 121 includes a first restrictor 125 and the second branch 122 includes a second restrictor 126, each of which is configured to restrict flow of the first mobile phase component, thereby providing the first and second portions of the first mobile phase component, respectively. Similarly, the third branch 123 includes a third restrictor 127 and the fourth branch 124 includes a fourth restrictor 128, each of which is configured to restrict flow of the second mobile phase component, thereby providing the first and second portions of the second mobile phase component, respectively. As would be apparent to one of ordinary skill in the art, the first and second branched flows of their respective first and second mobile phase components may alternatively be actively provided by one or more pumps providing the respective branch flows rather than passive division from common pumps with restrictions.

The relative levels of restriction dictate the proportioning or amount of the second mobile phase component (e.g., the strong solvent) that flows through each of the third and fourth branches 123 and 124. For example, the third restrictor 127 may be significantly less restrictive than the fourth restrictor 128, in which case the majority of the second mobile phase component flow (e.g., about 95 percent) contributed to the mobile phase passes through the third branch 123 (as the first portion of the second mobile phase component), while the remainder of the second mobile phase component flow (e.g., about 5 percent) passes through the fourth branch 124 (as the second portion of the second mobile phase component). The relative proportions between the first and second portions of the mobile phase components may vary to provide unique benefits for any particular situation or to meet application specific design requirements of various implementations, as would be apparent to one skilled in the art.

The proportioned flow into the input junction 131 and into the injection unit 130 changes the time for the sample to be motivated into the output junction 132. As the flow through either of the first or third branches 121 or 123 increases, the time to move the sample decreases as it is the flow rate of this combined stream that determines the rate of flow into subsequent adjoining streams. Concomitant with this decrease in loading time is an increase in the instantaneous proportion of sample and strong solvent (relative to weak solvent) that reaches the separation unit 140. The minimum total solvent load into the separation unit 140 occurs when the flow through first branch 12) is zero. Any increase in flow rate proportioned through the first branch 121, decreases the injection load time and increases the proportion of total solvent flow during injection by the rate of flow through first branch 121. The ability to match sample loading time, and total solvent concentration during injection, to the chromatographic speed of the separation unit 140 and mobile phase composition allows the maximum focusing of the injected sample on the head of the separation unit 140, thus allowing maximum chromatographic resolution.

For example, the first portion may be within a range of about 35 percent to about 100 percent and the second portion may be within a range of about 0 percent to about 65 percent of the second mobile phase component output by the second pump 112. When the second mobile phase component is the strong solvent, the first portion of the second mobile phase component is typically larger than the first portion of the first mobile phase component (at the input junction 131) in order to increase the flow rate of the combined stream through the injection unit 130. However, in cases where the sample solvent has much higher solvent strength than the strong (elution) solvent, the relative proportion of the second portion of the second mobile phase component (and/or the relative proportion of the second portion of the first mobile phase component) may be increased to lower the effect of the solvent strength the sample imparts as it reaches the head of the separation unit 140.

Similarly, the relative levels of restriction dictate the amount of the first mobile phase component (e.g., the weak solvent) that flows through each of the first and second branches 121 and 122. For example, the first restrictor 125 may be significantly more restrictive than the second restrictor 126, in which case the majority of the first mobile phase component flow (e.g., about 95 percent) contributed to the mobile phase passes through the second branch 122 (as the second portion of the second mobile phase component), white the remainder of the first mobile phase component flow (e.g., about 5 percent) passes through the first branch 121 (as the first portion of the first mobile phase component). Of course, the relative proportions between the first and second portions of the first mobile phase component may vary to provide unique benefits for any particular situation or to meet application specific design requirements of various implementations, as would be apparent to one skilled in the art. For example, the second portion may be within a range of about 65 percent to about 100 percent and the first portion may be within a range of about 0 percent to about 35 percent of the first mobile phase component output by the first pump system 111.

When the first mobile phase component is the weak solvent, the second portion of the first mobile phase component is typically larger than the second portion of the second mobile phase component (at the output junction 132) in order to further dilute the sample-containing stream output from the injection unit 130. The amount of dilution adjusts both the loading capacity of the separation unit 140 of the chromatography system 100 and the load speed by affecting the flow rate of the combined stream from the input junction 131. For example, increasing dilution by an increased proportion of the second portion of the first mobile phase component flowing through the second branch 122 tends to decrease the flow rate of the combined stream through the injection unit 130 as the sample-containing stream. Conversely, lowering the overall flow rate through the injection unit 130 reduces the instantaneous amount of sample solvent exiting the output junction 132, thus tending to decrease sample smearing within the sample separation unit 140 and to increase resolution of the separation results.

Figure 3:
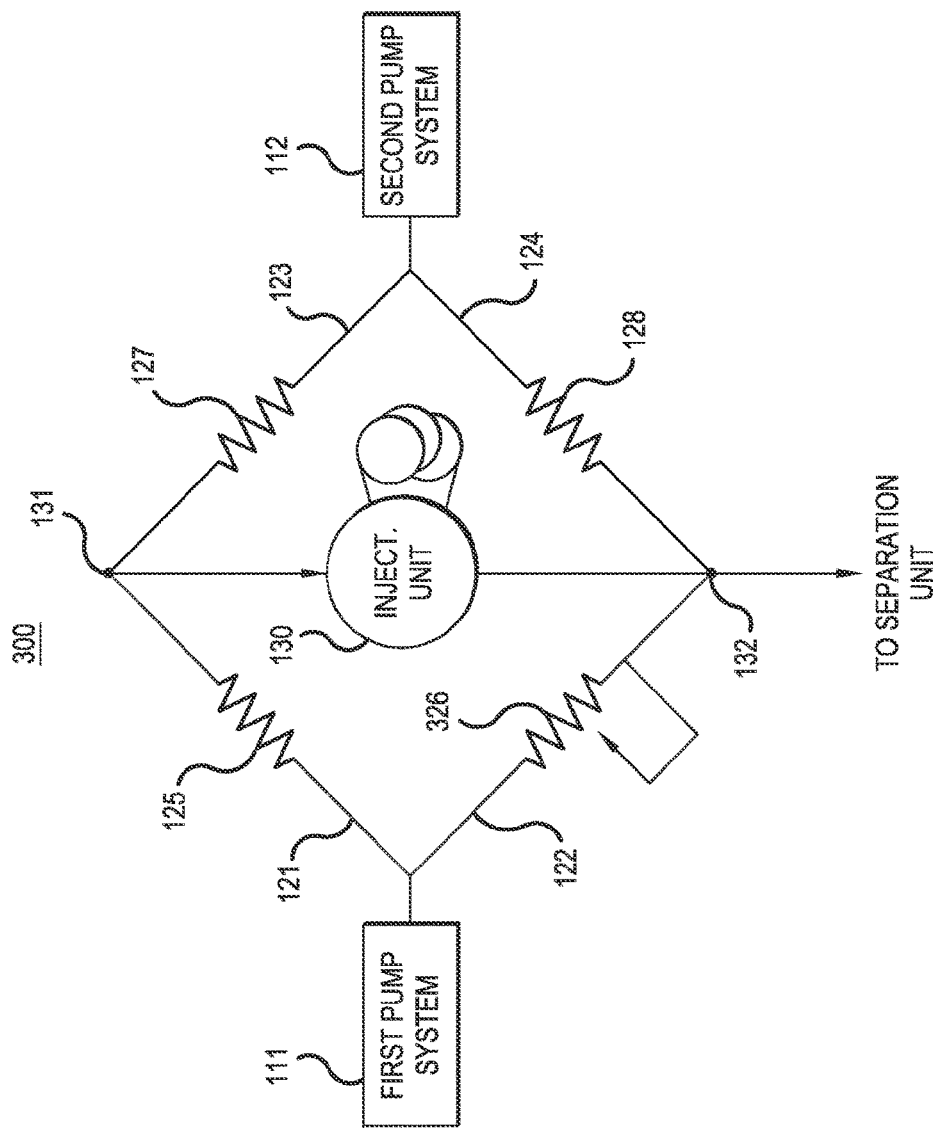
FIG. 3 is a simplified block diagram of a mobile phase bridge apparatus in a chromatography system, according to another representative embodiment.

FIG. 3 is a simplified block diagram of a mobile phase bridge apparatus in a chromatography system, according to another representative embodiment.

Referring to FIG. 3, mobile phase bridge apparatus 300 is substantially the same as mobile phase apparatus 200 in FIG. 2, except that a restriction of at least one of the first through fourth restrictors is variable. In the depicted embodiment, in particular, the mobile phase apparatus 300 includes first branch 121 with first restrictor 125, third branch 123 with third restrictor 127, and fourth branch 124 with fourth restrictor 128, as discussed above. However, the second branch 122 includes a variable restrictor 326, which is configured to variably restrict the flow of the second portion of the first mobile phase component. Because the variable restrictor 326 is in the second branch 122 in the depicted example, changes to the amount of restriction imposed by the variable restrictor 326 directly adjust the amount of dilution of the diluted sample-containing stream provided to the separation unit 140. That is, assuming that the first mobile phase component is the weak solvent, decreasing the restriction of the variable restrictor 326 (thereby increasing flow of the second portion of the first mobile phase component) increases the amount of dilution of the diluted sample-containing stream, while increasing the restriction of the variable restrictor 326 (thereby decreasing flow of the second portion of the first mobile phase component) decreases the amount of dilution of the diluted sample-containing stream.

The variable restrictor 326 may be implemented using an adjustable flow valve, for example. Examples of adjustable flow valves exemplarily include rotary valves with multiple parallel passages that can be added into the stream with valve rotation, rotary valves with an adjustable rotor passage between stator ports, or simply a selection valve capable of addressing a restriction from multiple restrictors. Also, in various embodiments, the variable restrictor 326 may be connected to the processing unit 160. In this case, the processing unit 160 may automatically control the amount of restriction of the variable restrictor 326 using a feedback system or pre-specified selection. For example, the processing unit 160 may monitor the loading of the separation unit 140 or the chromatographic resolution by monitoring detection unit 150 and/or the flow rate of the combined stream entering the injection unit 130, and adjust the amount of restriction of the variable restrictor 326 to obtain target values of these parameters. For example, if the flow rate of the sample-containing stream is excessive, the processing unit 160 may send a control signal to the variable restrictor 326 to decrease restriction, so that more of the second portion of the first mobile phase is provided following the injection unit 130. This, in turn, decreases the amount of the first portion of the first mobile phase, thereby decreasing the flow rate of the combined stream through the injection unit 130. Alternatively, or in addition, the variable restrictor 326 may be adjusted manually by the user.

In alternative embodiments, one or more of the first restrictor 125, the third restrictor 127 and the fourth restrictor 128 may be variable, in addition to the variable restrictor 326 or instead of the variable restrictor 326, without departing from the scope of the present teachings. For example, in an embodiment, the first restrictor 125 in the first branch 121 may be a variable restrictor, which is configured to variably restrict flow of the first portion of the first mobile phase component provided by the first pump system 111. Changes to the amount of restriction imposed by the first restrictor 125 being variable adjust the mix of the combined stream input to the injection unit 130. That is, decreasing the restriction of the first restrictor 125 (thereby increasing flow of the first portion of the first mobile phase component) increases the proportion of weak solvent in the combined stream and increases the flow rate of the combined stream through the injection unit 130, which results is a decrease in sample loading time. Of course, in various embodiments, if the first restrictor 125 were a variable restrictor, it may be connected to and controlled by the processing unit 160, as discussed above.

Figure 4:
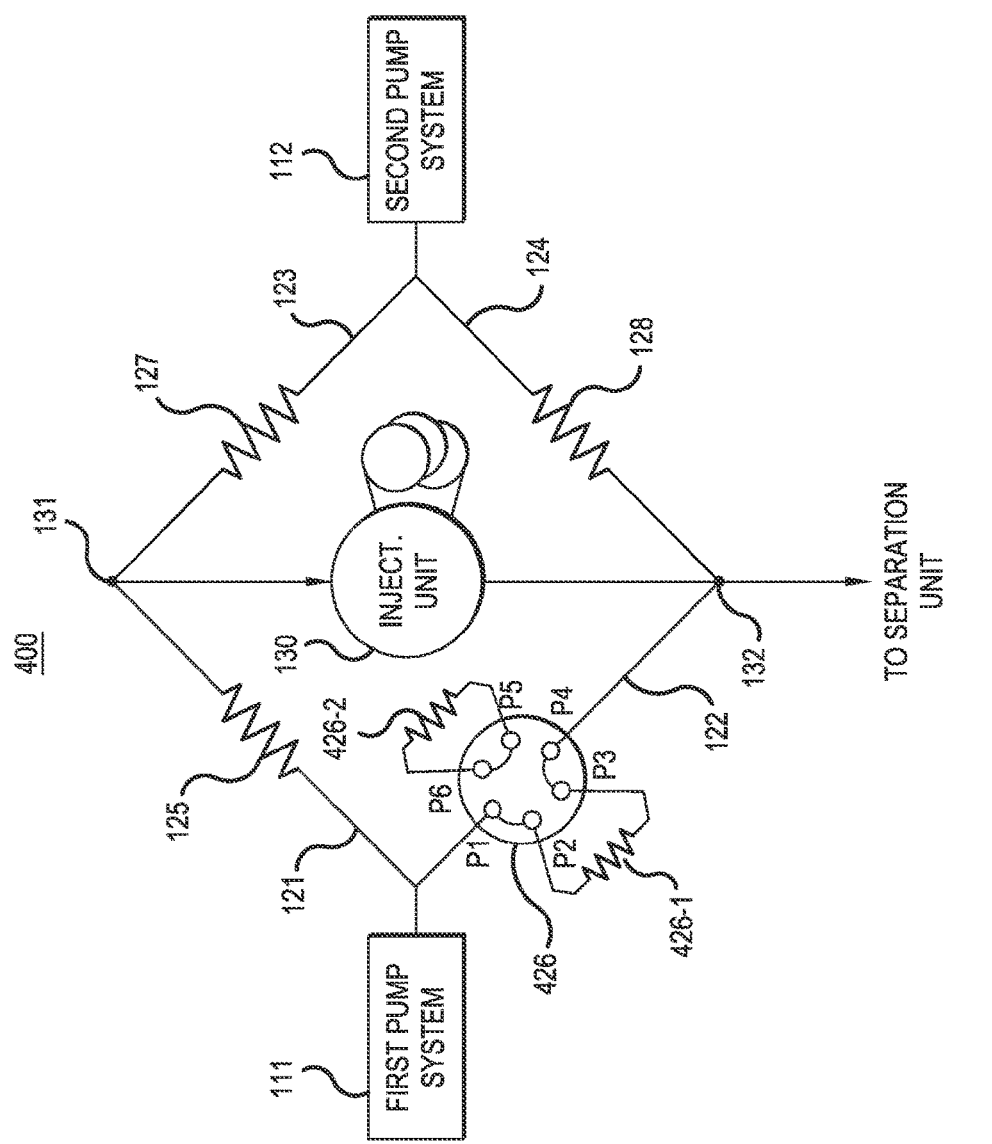
FIG. 4 is a simplified block diagram of mobile phase bridge apparatus in a chromatography system, according to another representative embodiment.

FIG. 4 is a simplified block diagram of a mobile phase bridge apparatus in a chromatography system, according to another representative embodiment.

Referring to FIG. 4, mobile phase apparatus 400 is substantially the same as mobile phase apparatus 200 in FIG. 2, except that a restriction of at least one of the first through fourth restrictors is selectable among a predetermined number of different restrictions. In the depicted embodiment, the mobile phase apparatus 400 includes first branch 121 with first restrictor 125, third branch 123 with third restrictor 127, and fourth branch 124 with fourth restrictor 128, as discussed above. However, second branch 122 includes a selectable restrictor 426, which is configured to enable selection between two predetermined levels of restriction for restricting flow of the second portion of the first mobile phase component. As stated above, because the selectable restrictor 426 is in the second branch 122 in the depicted example, changes to the amount of restriction imposed by the selectable restrictor 426 directly adjust the amount of dilution of the diluted sample-containing stream provided to the separation unit 140.

In the depicted embodiment, the selectable restrictor 426 is a two position, six port switching valve that enables switching between first restriction 426-1 and second restriction 426-2, although valving with additional positions for providing additional restriction alternatives may be included without departing from the scope of the present teachings. For purposes of illustration, the first restriction 426-1 may be less than the second restriction 426-2, such that selection of the first restriction 426-1 increases the flow of the second portion of the first mobile phase component, thereby increasing dilution of the diluted sample-containing stream. For example, selecting the first restriction 426-1 may result in about 90 percent of the first mobile phase component flow passing through the second branch 122, whereas selecting the second restriction 426-2 may result only about 75 percent of the second mobile phase component flow passing through the second branch 122.

In the depicted configuration, the second portion of the first mobile phase component flow enters and exits the selectable restrictor 426 through first port P1 and fourth port P4, respectively. The first restriction 426-1 is connected between second port P2 and third port P3, and the second restriction 426-2 is connected between fifth port P5 and sixth port P6. As shown in the example of FIG. 4, the first restriction 426-1 has been selected (e.g., automatically by the processing unit 160 or manually by the user or by some combination of both). In this case, the first port P1 is selectively coupled to the second port P2, and the third port P3 is selectively coupled to the fourth port 94 to create a path from the first pump system 111 to the output junction 132, thereby providing the second branch 122. If the second restriction 426-2 were to be selected, the first port P1 would be selectively coupled to the sixth port P6, and the fifth port P5 would be selectively coupled to the fourth port P4 to create the path through the second branch 122 from the first pump system 111 to the output junction 132. Of course, other port arrangements and/or other types of switching or restriction selection devices may be incorporated without departing from the scope of the present teachings.

Because the selectable restrictor 426 is in the second branch 122 in the depicted example, changes to the amount of restriction imposed by the selectable restrictor 426 directly adjust the amount of dilution of the diluted sample-containing stream provided to the separation unit 140, as discussed above. Also, in various embodiments, the selectable restrictor 426 may be connected to the processing unit 160, in which case the processing unit 160 may automatically select one of the first or second restrictions 426-1 and 426-2 using a feedback system, as discussed generally above, Alternatively, or in addition, the selectable restrictor 426 may be switched manually by the user.

In alternative embodiments, one or more of the first restrictor 125, the third restrictor 127 and the fourth restrictor 128 may be selectable restrictors, in addition to or instead of the selectable restrictor 426, without departing from the scope of the present teachings. Additional selectable restrictors may have the same or different numbers of available restrictions, as well as the same or different levels of restriction. Of course, the number of selectable restrictors and corresponding locations and available restrictions may vary to provide unique benefits for any particular situation or to meet application specific design requirements of various implementations, as would be apparent to one skilled in the art.

Figure 5:
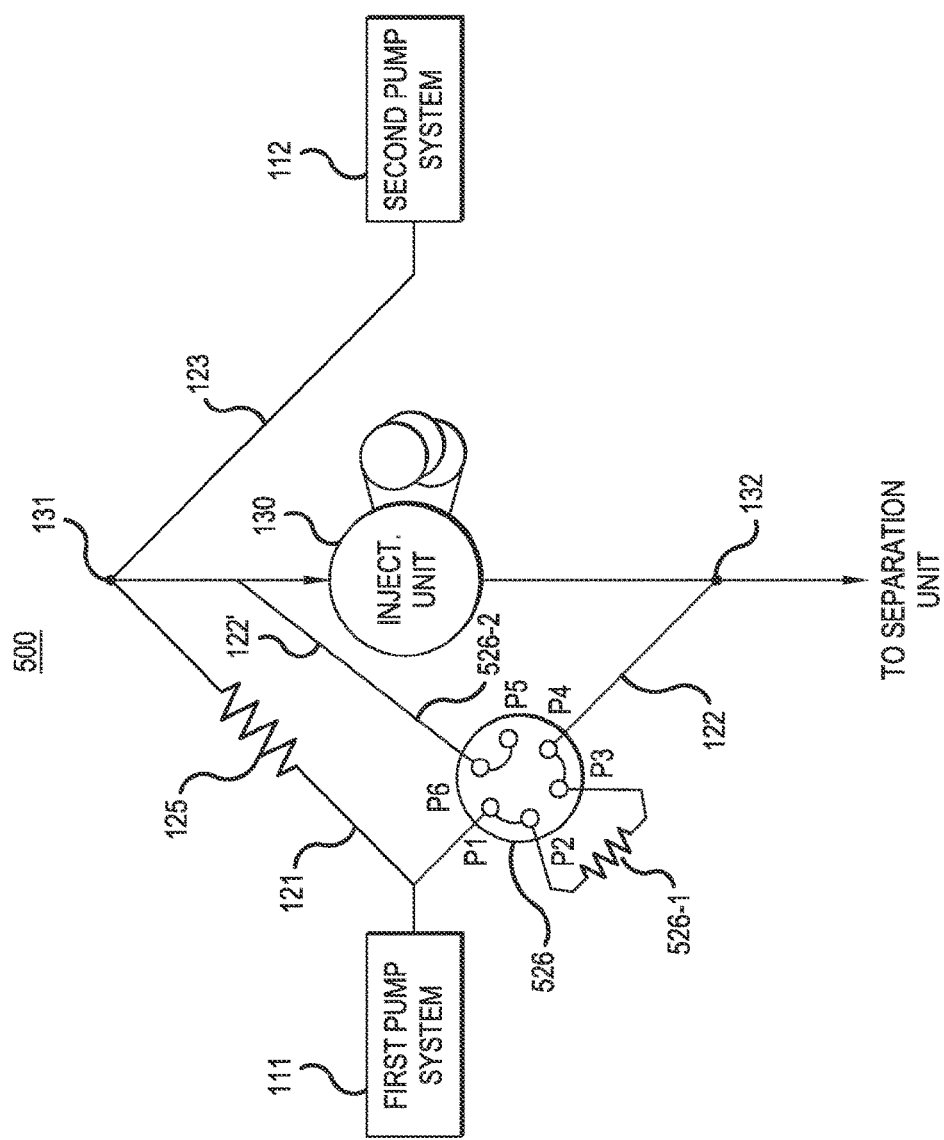
FIG. 5 is a simplified block diagram of a mobile phase bridge apparatus in a chromatography system, according to another representative embodiment.

FIG. 5 is a simplified block diagram of a mobile phase bridge apparatus in a chromatography system, according to another representative embodiment.

Referring to FIG. 5, mobile phase apparatus 500 is substantially similar to the mobile phase apparatus 200 in FIG. 2, except that a restriction of at least one of the first through fourth restrictors is selectable between a restriction and a path altering the course a corresponding branch. Also, one of the branches is effectively blocked or removed. In the depicted embodiment, in particular, the mobile phase apparatus 500 includes first branch 121 with first restrictor 125, second branch 122 with a selectable restrictor 526, third branch 123 with no restrictor, and no fourth branch 124. Removal of the fourth branch 124 results of the second mobile phase component flowing through the third branch 123 to the input junction 131, and otherwise prevents any portion of the second mobile phase component from directly affecting the dilution of the diluted sample-containing stream at the output junction 132. The fourth branch 124 may be removed, as a practical matter, by providing a very high restriction fix the fourth restrictor 128, for example, resulting in no flow of the second portion of the second mobile phase component. By avoiding any strong solvent dilution, when the second pump system 112 is providing the strong solvent, for example, the lowest total solvent load is provided upon injection. That is, the portion of strong solvent provided by the third branch 123 provides for displacement of the sample and sample solvent without additively combining through the fourth branch. In alternative configurations, the fourth branch 124 may be included as discussed above with regard to other embodiments.

Meanwhile, similar to FIG. 4, above, the second branch 122 includes a selectable restrictor 526. However, the selectable restrictor 526 is configured to enable selection between a restriction 526-1 for restricting flow of the second portion of the first mobile phase component through the second branch 122, and an alternative path 526-2 that redirects the second branch through an alternate second branch 122' to direct the second portion of the first mobile phase to the input of the injection unit 130. As stated above, because the selectable restrictor 526 is in the second branch 122 in the depicted example, selecting the restriction 526-1 directly adjusts the dilution of the diluted sample-containing stream provided to the separation unit 140. However, selection of the alternative path 526-2 indirectly affects the dilution of the diluted sample-containing stream by essentially diverting the entire first flow stream from the first pump system 111 to the combined stream from the input junction 131 input to the injection unit 130. When the alternate second branch 122' is selected, the entire mobile phase from both the first and second pumps 111 and 112, respectively, is directed into the combined stream. This results in essentially standard injection with the fastest possible sample loading. This embodiment exemplifies one of the means of providing an adjustable sample loading time varying from the fastest cycle time, to a diluted injection spread out over a longer time, by selecting an appropriate flow rate of the combined stream through injection unit 130.

In the depicted embodiment, the selectable restrictor 526 is a two position, six port switching valve that enables switching between the restriction 526-1 and the alternative path 526-2, although valves with additional positions for providing additional restriction and/or path alternatives may be included without departing from the scope of the present teachings. For purposes of illustration, the restriction 526-1 may result in about 90 percent of the first mobile phase component flow passing through the second branch 122, whereas selecting the alternative path 526-2 redirects that percentage of the first mobile phase component flow to the input of the injection unit 130 (after mixing with the combined stream from the input junction 131).

In the depicted configuration, the second portion of the first mobile phase component flow enters the selectable restrictor 526 through first port P1, and exits the selectable restrictor 526 through one of fourth port P4 or sixth port P6. The restriction 526-1 is connected between second port P2 and third port P3, and the alternative path 526-2 is connected to the sixth port P6. Fifth port P5 may be plugged. As shown in the example of FIG. 5, the restriction 526-1 has been selected (e.g., automatically by the processing unit 160 or manually by the user or by some combination of both). In this case, the first port P1 is selectively coupled to the second port P2, and the third port P3 is selectively coupled to the fourth port P4 to create a path through the second branch 122 from the first pump system 111 to the output junction 132. If the alternative path 526-2 were to be selected, the first port P1 would be selectively connected to the sixth port P6, from which the second portion of the first mobile phase component would be directed to the input of the injection unit 130, and mixed with the first portion of the first mobile phase component and the first portion of the second mobile phase component, previously mixed at the input junction 131. Of course, other port arrangements and/or other types of valves or restriction selection devices may be incorporated without departing from the scope of the present teachings. The shunting arrangement of alternate second branch 122' is functionally equivalent to having the switching valve uncouple restrictor 526-1 and block the second branch 122.

Figure 6:
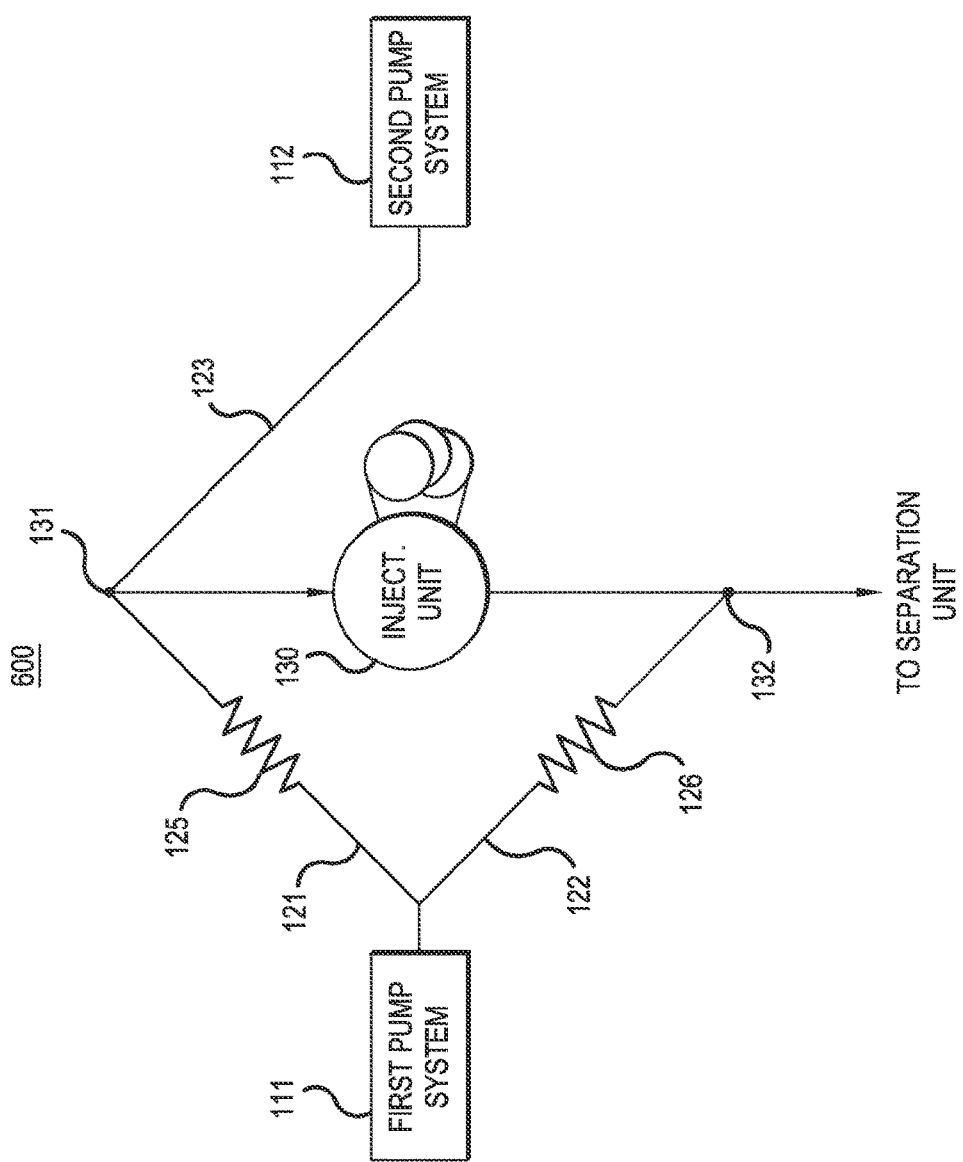
FIG. 6 is a simplified block diagram of a mobile phase bridge apparatus in a chromatography system, according to another representative embodiment.

FIG. 6 is a simplified block diagram of a mobile phase bridge apparatus in a chromatography system, according to another representative embodiment.

Referring to FIG. 6, mobile phase apparatus 600 is substantially similar to the mobile phase apparatus 200 in FIG. 2, except that fourth branch 124 is effectively blocked or removed. In the depicted embodiment, in particular, the mobile phase apparatus 600 includes first branch 121 with first restrictor 125, second branch 122 with second restrictor 126, third branch 123 with no restrictor, and no fourth branch 124. As discussed above, removal of the fourth branch 124 results in all of the second mobile phase component flowing through the third branch 123 to the input junction 131, and otherwise prevents any portion of the second mobile phase component from directly affecting the dilution of the diluted sample-containing stream at the output junction 132. The fourth branch 124 may be removed, as a practical matter, by providing a very high restriction for the fourth restrictor 128, for example, resulting in no flow of the second portion of the second mobile phase component.

With regard to the remaining restrictors, first restrictor 125 and second restrictor 126, it is understood that they may be implemented as fixed restrictions, as shown. Or, one or both may be implemented as a variable restrictor, as discussed above with reference to FIG. 3, or a selectable restrictor, as discussed above with reference to FIG. 4.

Figure 7:
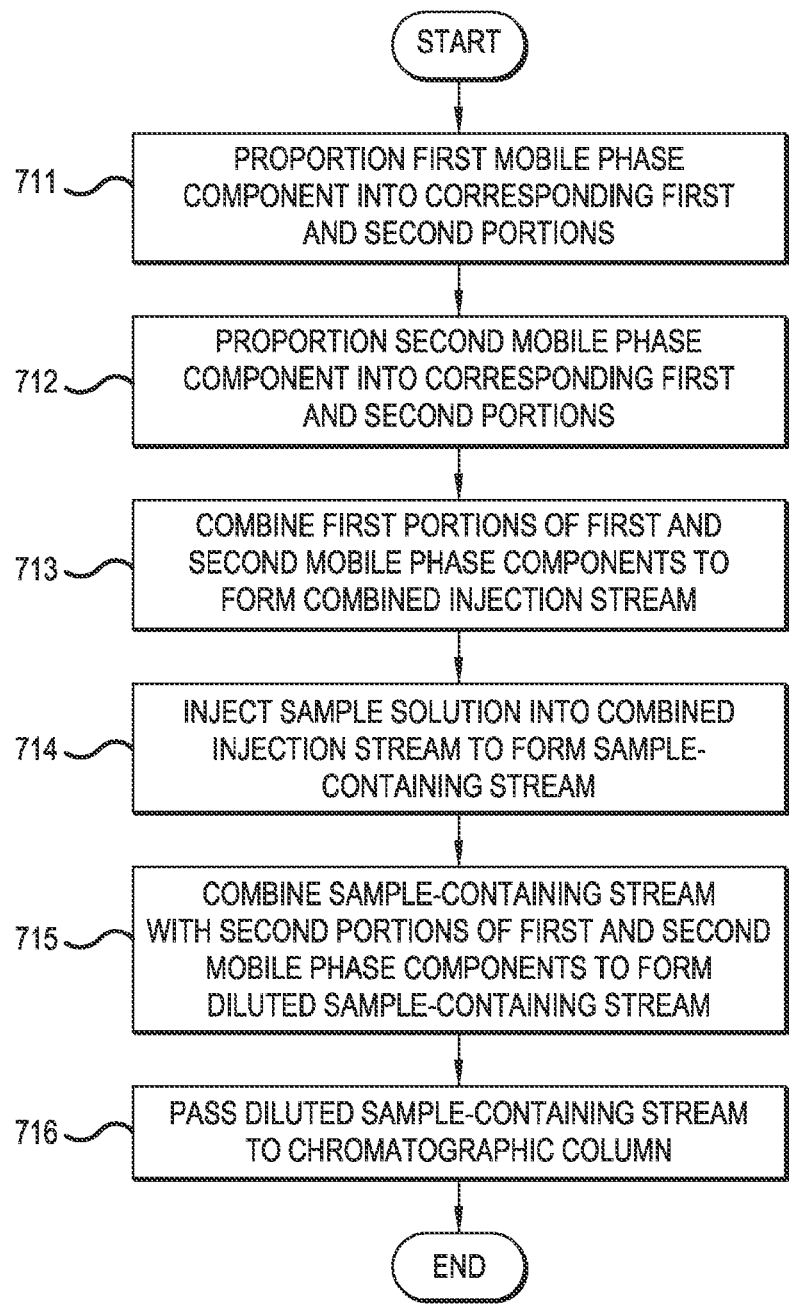
FIG. 7 is a flow diagram of a method for injecting a sample in a chromatography system, according to a representative embodiment.

FIG. 7 is a flow diagram of a method for injecting a sample in a chromatography system, according to another a representative embodiment.

Referring to FIG. 7, the chromatography system has a mobile phase, as discussed above, comprising a first mobile phase component and a second mobile phase component provided by first and second pump systems 111 and 112, respectively. In block S711, the first mobile phase component is proportioned into corresponding first and second portions of the first mobile phase component, and in block S712 the second mobile phase component is proportioned into corresponding first and second portions of the second mobile phase component.

The first portion of the first mobile phase component and the first portion of the second mobile phase component are combined to forma combined stream and directed to an injection unit in block S713. The first portions of the first and second mobile phase components may be combined at the input junction 131, for example. A sample solution is injected into the combined stream in block S714 to form a sample-containing stream.

In block S715, the sample-containing stream is combined with the second portion of the first mobile phase component and the second portion of the second mobile phase component to form a diluted sample-containing stream. The sample-containing stream and the second portions of the first and second mobile phase components may be combined at the output junction 132, for example. Alternatively, the sample-containing stream may be combined with one of the second portion of the first or second mobile phase component, and subsequently combined with the other one of the second portion of the first or second mobile phase component at different junctions, for example. The diluted sample-containing stream is passed to a chromatographic column in block S716 for separating the sample constituents. In an embodiment, the method may further include varying the second portion of the first mobile phase component (and/or the second portion of the second mobile phase component) to adjust an amount of dilution of the diluted sample-containing stream. The varying of either portion of either mobile phase component may be performed in real-time.

As mentioned above, the mobile phase bridge apparatus, including mobile phase delivery apparatus and sample introducing apparatus, according to the various representative embodiments may be incorporated into different types of types of chromatography systems, including SFC, normal phase HPLC and reverse phase HPLC. Likewise, the mobile phase bridge apparatus may be incorporated into a two-dimensional (2D) chromatography system, in which peaks collected by a first chromatography system (first dimension) are further separated and detected by a second chromatography system (second dimension). The first and second chromatography systems may be different from one another. For example, the first chromatography system may be a reverse phase HPLC system and the second chromatography system may be an SFC system. In this 2D chromatography system, the injection technique disclosed below may be referred to as peak concentrating solventless injection.

Among other uses, 2D chromatography enables further detection of co-eluting peaks. For example, a reverse phase HPLC system (first dimension) may capture chiral molecules, resulting in a chiral peak, but is otherwise incapable of separating the mirror image, right and left-hand enantiomers of the chiral molecules. Accordingly, the compounds producing the co-eluting peak may be provided to an SFC system (second dimension), which is capable of detecting and generating peaks corresponding to each enantiomer. However, the injection of large volumes of the mobile phase of the HPLC system is inherently incompatible with a SFC system, and therefore must be removed through a transitional unit, e.g., comprising a predetermined sequence of switching and purging steps by operation of multiple valves, as discussed below. For example, water (which is a polar solvent) may be the weak solvent in a reverse phase HPLC separation, but would behave as a strong solvent, owing to its polarity, in an SEC separation. Thus, the water cannot be incorporated as the weak solvent in the SEC system. Further, regardless of solvent compatibility, the shear volume of the first dimension mobile phase (weak and strong solvents) in an HPLC system far exceeds that of the practical injection volumes on an SFC system used as second dimension. The bulk of the first dimension mobile phase must therefore be removed for injection into the second dimension mobile phase of the SFC system to enable the 2D chromatography by the transitional unit.

Figure 8A:
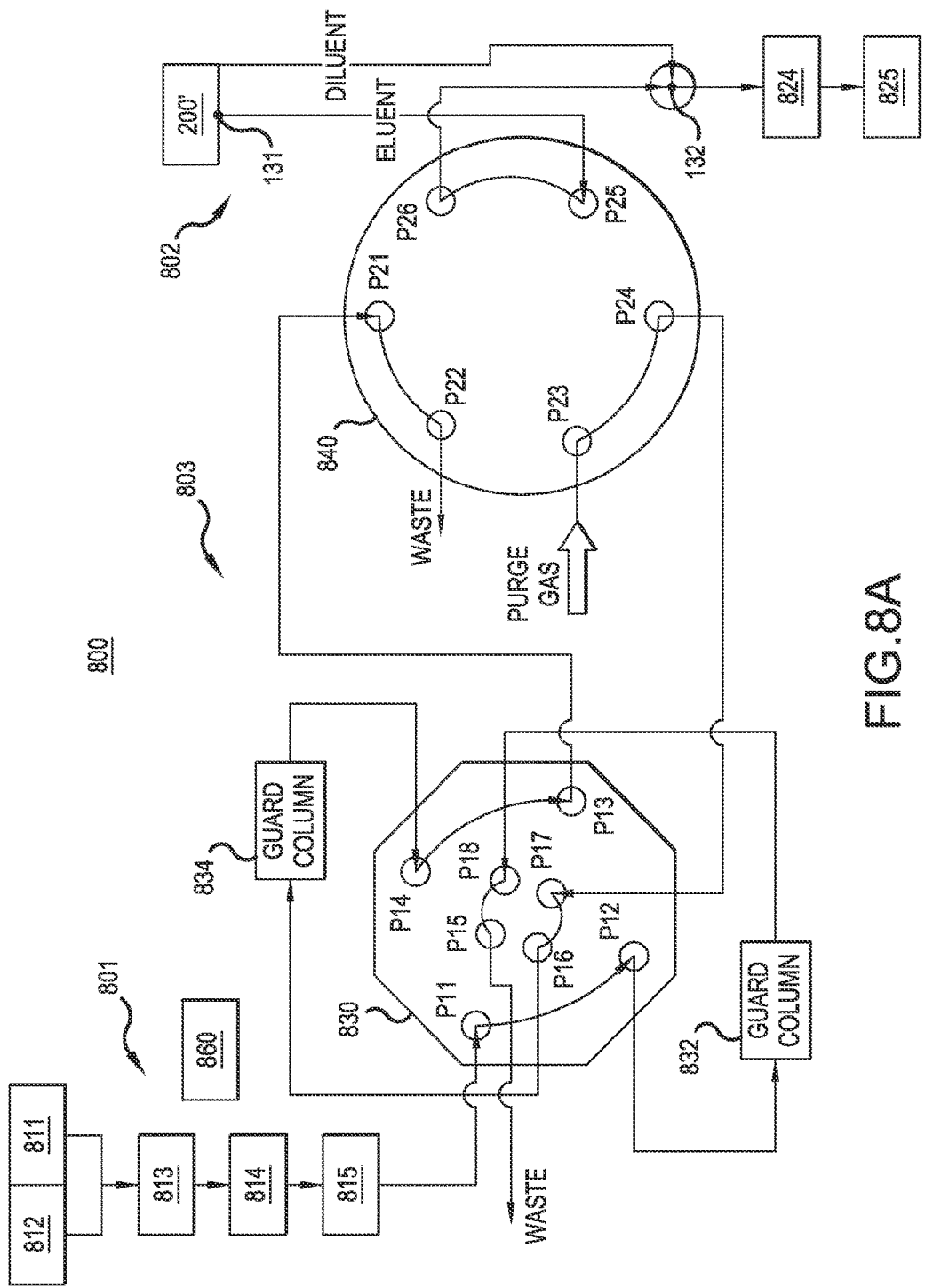
FIG. 8A is a simplified block diagram of a 2D chromatography system including a mobile phase bridge apparatus, according to a representative embodiment.
Figure 8B:
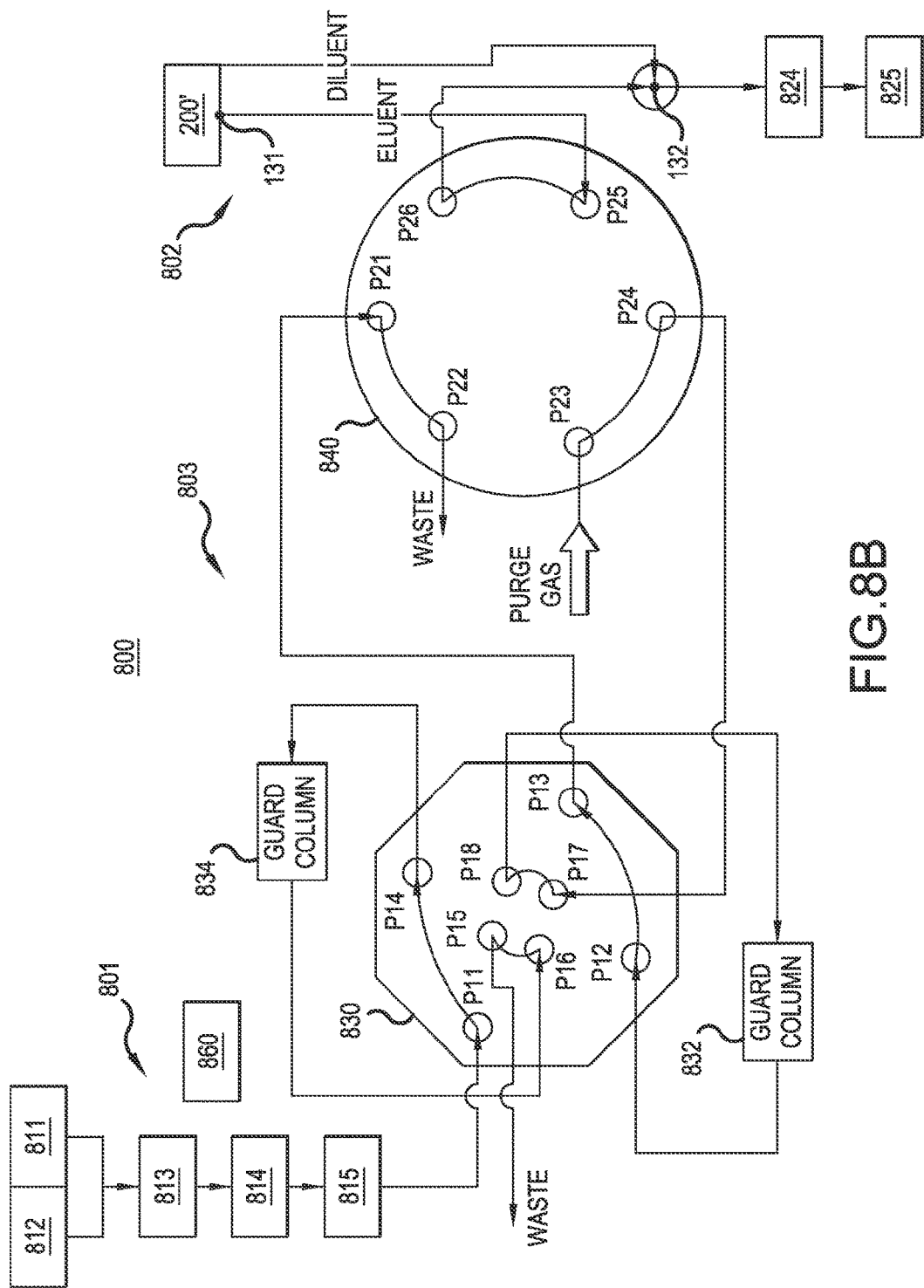
FIG. 8B is another simplified block diagram of the 2D chromatography system illustrated in FIG. 8A, according to a representative embodiment.
Figure 8C:
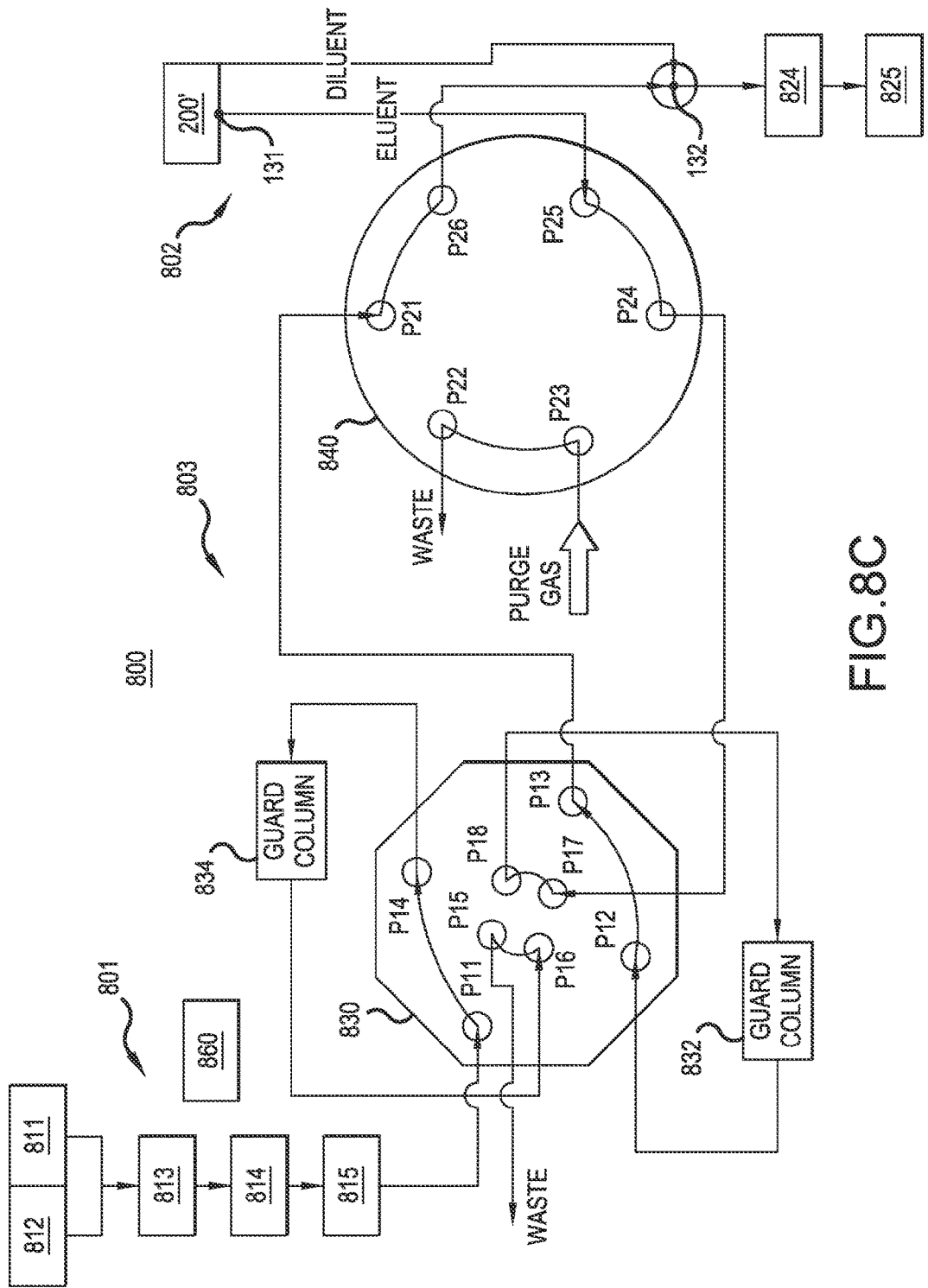
FIG. 8C is another simplified block diagram of the 2D chromatography system illustrated in FIG. 8A, according to a representative embodiment.

FIGS. 8A-8C are simplified block diagrams of a 2D chromatography system including a mobile phase bridge apparatus, according to a representative embodiment. FIG. 8A, FIG. 8B, FIG. 8C demonstrate three successive operations employed to collect a peak in a first chromatography system 801, remove much of the first dimensional mobile phase, and perform a focused introduction of peak constituents into a second dimension flow stream respectively.

Referring to FIG. 8A, 2D chromatography system 800 includes first chromatography system (or first dimension) 801, second chromatography system (or second dimension) 802, and transitional unit 803 for transitioning aliquots of column effluent between the first and second dimensions. For purposes of illustration, the first chromatography system 801 is a reverse phase HPLC system and the second chromatography system 802 is a SFC system, as mentioned above, although different types of chromatography systems may be incorporated without departing from the scope of the present teachings.

The first chromatography system 801 includes first and second pump systems 811 and 812 for providing weak solvent and strong solvent, respectively, as discussed above with reference to the first and second pump systems 111 and 112. The first chromatography system 801 further includes a sample introducing apparatus 813 (e.g., such as an injector valve), a separation unit 814 (e.g., such as a chromatographic column) and a detection unit 815, which may be substantially the same as the mobile phase delivery apparatus 110, sample introducing apparatus 120, the separation unit 140 and the detection unit 150 discussed above with reference to FIG. 1, for example. A fluid stream containing separated sample constituents or compounds is output by the separation unit 814, and peaks corresponding to the separated compounds are detected by the detection unit 815, where the magnitude of each peak correlates to the amount of the corresponding compound in the sample. The fluid stream containing the separated compounds (which may be referred to as the first dimension mobile phase) continues to flow from the detection unit 815 to the transitional unit 803. Aspects of transitional unit 803, with regard to the first chromatography system 801, are substantially the same as fraction collection unit 170 of FIG. 1.

The chromatography system 800 may further include a processing unit 860 configured to control operations of one or more of the first and second pump systems 811 and 812, the sample introducing apparatus 813, the separation unit 814 and the detection unit 815. In various embodiments, the processing unit 860 may further control operations of first and second valves 830 and 840 of the transitional unit 803, and/or operations of the second chromatography system 802 (including mobile phase bridge apparatus 200', e.g., in place of processing unit 160), discussed below. The processing unit 860 may be implemented substantially the same as the processing unit 160 discussed above with regard to FIG. 1. For the sake of convenience, the various connections between the processing unit 860 and components of the first chromatography system 801, the second chromatography system 802, and/or the transitional unit 803 are not expressly depicted in the FIGS. 8A-8C, although it is understood that any type of wired and/or wireless connections enabling control communications may be incorporated without departing from the scope of the present teachings.

The transitional unit 803 transitions the compounds in portions of the fluid stream in which the peaks are detected from the first chromatography system 801 to the second chromatography system 802. In the depicted embodiment, the transitional unit 803 includes first valve 830, which may be an eight-port two position multi-dimension valve as shown, and second valve 840, which is a six-port two position injection valve. Thus, the first valve 830 includes first port P11 through eighth port P18, and the second valve 840 includes first port P21 through sixth port P26. The ports may be selectively coupled or connected to one another in various configurations within and across the first and second valves 830 and 840 to enable the desired paths for the different transitional phases. Although not shown in FIGS. 8A-8C (or in FIGS. 9A-9C), it is understood that other types and combinations of valves (e.g., 10 port and 6 port valves) may be incorporated as the first valve 830 (and 930), without departing from the scope of the present teachings.

The second chromatography system 802 includes a mobile phase bridge apparatus 200', which functions substantially the same as the mobile phase bridge apparatus 200 discussed above with reference to FIG. 2. However, it is understood that other embodiments of the mobile phase bridge apparatus, e.g., discussed above with reference to FIGS. 3-6, may be incorporated without departing from the scope of the present teachings. (Also, while not shown, embodiments of the mobile phase bridge apparatus may be incorporated into the first chromatography system 801, as well.) One difference, however, is that the mobile phase bridge apparatus 200' does not contain a specific injection unit, such as injection unit 130. Rather, the introduction of sample, or in the case of a 2D chromatography system an aliquot of the first dimension effluent, to the combined fluid stream is performed by second valve 840. The combined stream is termed as eluent, comprising the combination of the first portion of the weak solvent and the first portion of the strong solvent (from branches 121 and 123, respectively) from input junction 131 (e.g., shown in FIGS. 2-6) of the mobile phase bridge apparatus 200'. The second chromatography system 802 further includes a separation unit 824 (e.g., such as a chromatographic column) and a detection unit 825, which may be substantially the same as the separation unit 140 and the detection unit 150 discussed above with reference to FIG. 1. When the second chromatography system 802 is performing supercritical fluid chromatography with carbon dioxide as a mobile phase component, for example, detection unit 825 may be construed to fluidically connect to a back pressure regulator (not shown).

Referring to FIG. 8A, the first and second valves 830 and 840 are configured so that the fluid stream containing the separated compounds from the separation unit 814 and the detection unit 815 of the first chromatography system 801 flows through the first valve 830 to the guard column 832 for retaining compounds corresponding to peaks. In particular, the output of the detection unit 815 is connected to first port P11 of the first valve 830, which is coupled to the second port P12, which is connected to an input of the guard column 832. An output of the guard column 832 is connected to eighth port P18, which is coupled to fifth port P15 configured to output the fluid stream to waste. (Notably, throughout this disclosure, input and output of guard columns and holding loops are used subjectively, depending on the direction of fluid flow through the guard column or the holding loop at the time.)

In an embodiment, an (optional) additional pump system 816 may be used to selectively supply additional solvent to the flow stream after detection unit 815. The additional pump system 816 may be incorporated after the detection unit 815 and before the first valve 830 of the transitional unit 803, for example. An addition of weak solvent changes the composition ratio of strong and weak solvent, thus altering the partitioning of sample constituents to favor retention on the guard column 832 stationary phase. Thus, most of the sample compound is retained on the guard column 832, while the first dimension mobile phase is expelled to waste. Further, use of the additional pump system 816 enables an internal volume of the guard column 832 to be substantially less than the volumes of an analytical chromatographic column, such as separation unit 814. For example, the separation unit 814 may be a 4.6 mm×150 mm, 5μ, particle size, chromatographic column, for example, while the guard column 832, only needing the capacity of a separated peak, may be a 2.1 mm×12.5 mm, 3μ, particle size, chromatographic column.

Meanwhile, the guard column 834 is purged, for example, using a purge gas (e.g., carbon dioxide ($CO_2$) or nitrogen ($N_2$)) originating at third port P23 of the second valve 840 to displace residual solvent from the first dimension mobile phase remaining in guard column 834. The predominately weak solvent from the first dimension may act as strong solvent in the second dimension, and thus the amount of first dimension mobile phase is advantageously reduced ("dried") by purging. Effects of residual amounts not expelled from the guard column 834 by purging are mitigated by the dilution using the bridge injection principles disclosed herein. The third port P23 is coupled to fourth port P24, which is connected to seventh port P17 of the first valve 830. The seventh port P17 is coupled to sixth port P16, which is connected to an input of the guard column 834. An output of the guard column 834 is connected to fourth port P14, which is coupled to third port P13, which is connected to first port P21 of the second valve 840. The first port P21 is coupled to second port P22 configured to output the purged contents of the guard column 834 to waste.

When the detection unit 815 and/or processing unit 860 recognizes that a peak of interest has reached the guard column 832, the first valve 830 will be switched in order to move the guard column 832 out of the first chromatography system 801 (first dimension) into the second chromatography system 802 (second dimension), as shown in FIGS. 8B and 8C Referring to FIG. 8B, the guard column 832 is purged by the purge gas, which displaces the first dimension mobile phase from the guard column 832 to waste, when first valve 830 is switched. The purge gas originates at the third port P23 of the second valve 840, which is coupled to the fourth port P24, which remains connected to the seventh port P17 of the first valve 830. The seventh port P17 is switched to the eighth port P18, which is connected to an input of the guard column 832 for receiving the purge gas. An output of the guard column 832 is connected to the second port P12, which is switched to the third port P13 of the first valve 830, which remains connected to the first port P21 of the second valve 840. The purged contents (un-retained mobile phase) of the guard column 832 are output to waste from the first port P21 via the second port P22 of second valve 840. The purge gas displaces the first dimension mobile phase and "dries" the sample compounds corresponding to the detected peak resident on the guard column 832.

Meanwhile, when first valve 830 has switched the guard column 832 out of the first dimension flow stream, the fluid stream output by the detection unit 815 is redirected to the guard column 834 by via the first port P11 of the first valve 830, which is switched to the fourth port P14, which is connected to an input of the guard column 834. An output of the guard column 834 is connected to the sixth port P16, which is switched to the fifth port P15 configured to output the fluid stream to waste. The guard column 834 thus is positioned in the first chromatography system 801.

Referring to FIG. 8C, subsequent to the removal of first dimension mobile phase from guard column 832, the second valve 840 switches to pass the combined stream (which may be referred to as portions of the second dimension mobile phase) from the input junction 131 of the mobile phase bridge apparatus 200' into the guard column 832, in which the sample compounds are retained, thereby switching the guard column 832 into the second chromatography system 802. The sample compounds resident on guard column 832 are eluted from the guard column into the combined stream to provide a sample-containing stream, which is directed to the output junction 132 (e.g., shown in FIGS. 2-6). As discussed above, the combined stream may comprise a mixture of a first portion of a first mobile phase component from the first pump system 111 and a first portion of a second mobile phase component from the second pump system 112. At the output junction 132, the sample-containing stream is mixed with a diluent comprising second portion of the first mobile phase component from the first pump system 111 and any second portion of the second mobile phase component of the second pump system 112 to provide the diluted sample-containing stream input to the separation unit 824 (e.g., the second dimension chromatographic column). The separation unit 824 separates the compounds, which are detected by the detection unit 825 of the second chromatography system 802.

More particularly, the combined stream from the input junction 131 enters fifth port P25 of the second valve 840, which is switched to the fourth port P24, which remains connected to the seventh port P17 of the first valve 830. The configuration of the first valve 830 is unchanged between the configurations represented by FIGS. 8B and 8C. That is, the seventh port P17 remains coupled to the eighth port P18, which remains connected to an input of the guard column 832. An output of the guard column 832 remains connected to the second port P12, which remains coupled to the third port P13, which remains connected to the first port P21 of the second valve 840. The first port P21 is switched to connect to the sixth port P26 configured to output the sample-containing stream to the output junction 132. The output junction 132 provides the diluted sample-containing stream to the separation unit 824.

Meanwhile, when second valve 840 has switched guard column 832 into the second dimension flow stream, the purge gas is output to waste at the second port P22 directly from the third port P23 of the second valve 840. Also, the fluid stream output by the detection unit 815 of the first chromatography system 801 continues to be redirected to the guard column 834 via the first port P11 and the fourth port P14, and output from the guard column 834 to waste via the sixth port P16 and the fifth port P15.

After the compounds on the guard column 832 have been eluted into the second dimension flow stream, the second valve 840 may switch back to the configuration depicted in FIG. 8B. Accordingly, the fluid stream output by the detection unit 815 is directed to the guard column 834, awaiting detection of the next peak of interest when first valve 830 may switch placing guard column 834 in the second dimension flow stream. With the symmetry inherent in the configuration of the first valve 830, reference to the guard column 832 and the guard column 834 may be used alternatively in context of flow stream participation throughout this disclosure. When the first valve 830 is in the first of its two positions, the guard column 832 is in the first dimension flow stream and the guard column 834 is under the control of the second valve 840 and the second dimension flow stream. When the first valve 830 is in the alternate position, the guard column 834 is in the first dimension flow stream and the guard column 832 is under the control of the second valve 840, as discussed above. Also, as would be apparent to one of ordinary skill in the art, multiple guard columns, arranged in parallel, may be individually addressed by multi-position selection valving (not shown) for the concomitant retention and subsequent second dimension injection of multiple first dimension sample aliquots independent of second valve 840.

Figure 9A:
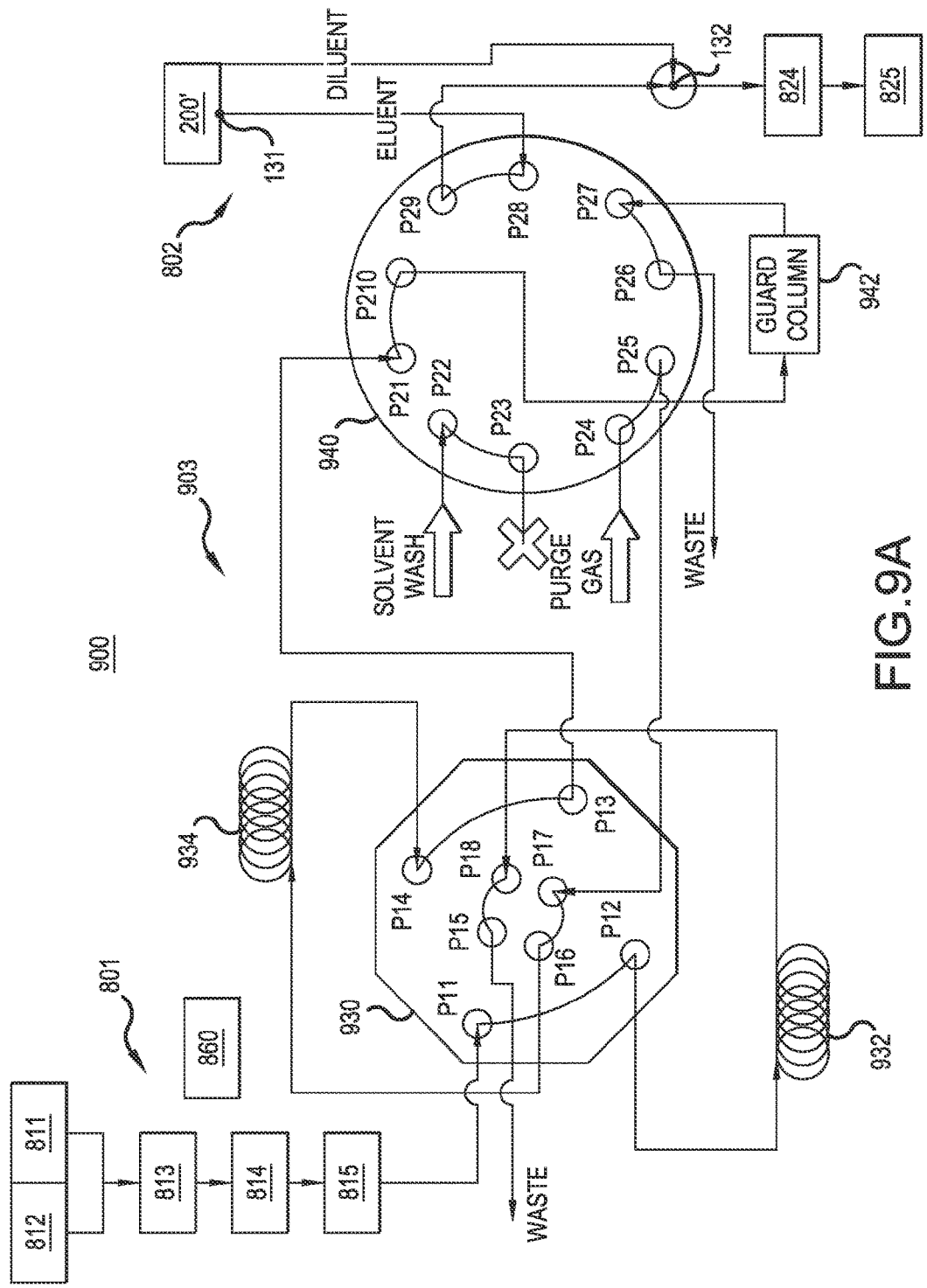
FIG. 9A is a simplified block diagram of a 2D chromatography system including a mobile phase bridge apparatus, according to a representative embodiment.
Figure 9B:
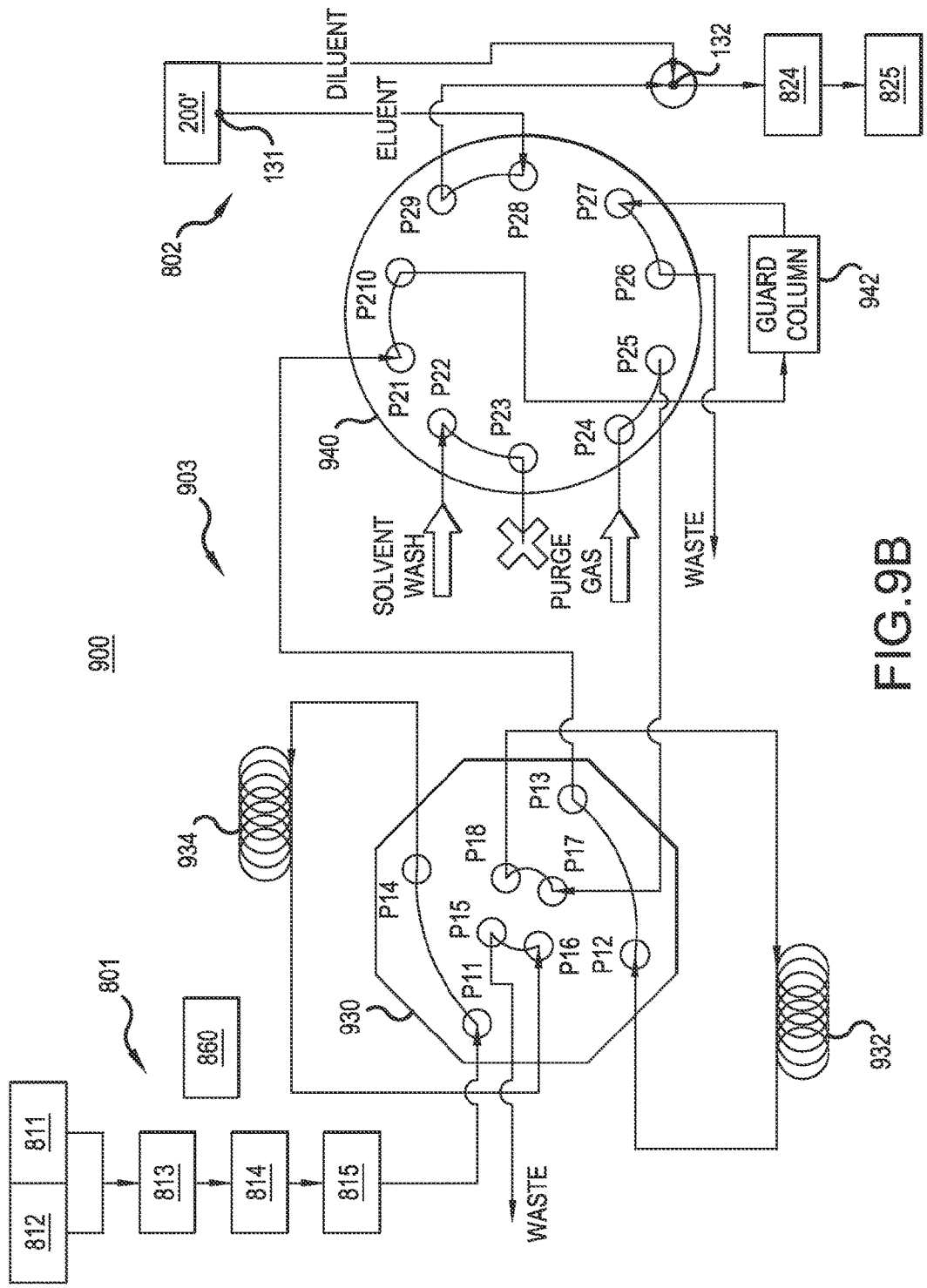
FIG. 9B is another simplified block diagram of the 2D chromatography system illustrated in FIG. 9A, according to a representative embodiment.
Figure 9C:
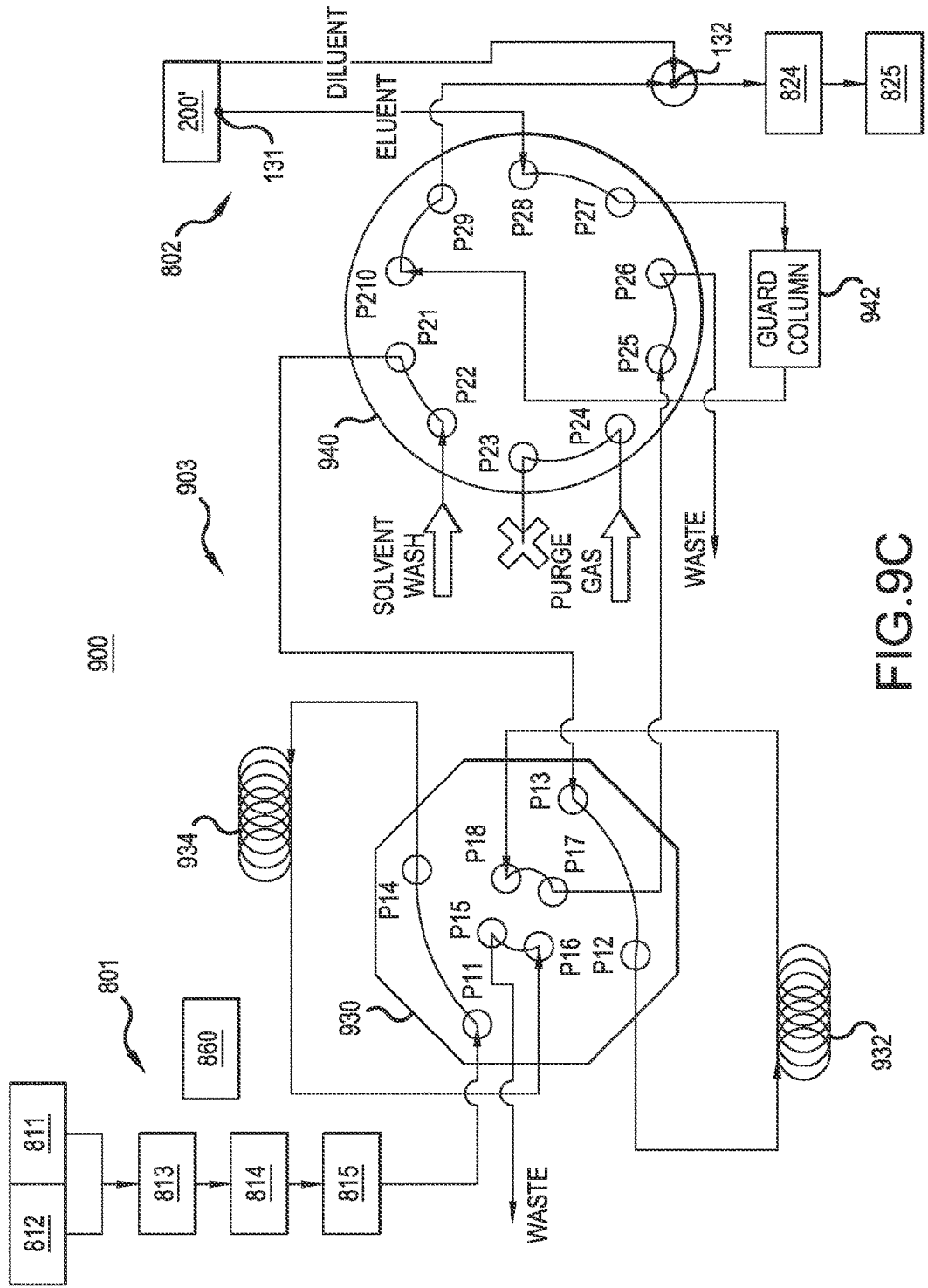
FIG. 9C is another simplified block diagram of the 2D chromatography system illustrated in FIG. 9A, according to a representative embodiment.

FIGS. 9A 9C are simplified block diagrams of a 2D chromatography system including a mobile phase bridge apparatus, according to another representative embodiment.

Referring to FIG. 9A, 2D chromatography system 900 includes first chromatography system (or first dimension) 801 and second chromatography system (or second dimension) 802, as discussed above with reference to FIGS. 8A-8C. The 2D chromatography system 900 further includes transitional unit 903 for transitioning between the first and second dimensions. For purposes of illustration, the first chromatography system 801 is a reverse phase HPLC system and the second chromatography system 802 is a SFC system, although different types of chromatography systems may be incorporated without departing from the scope of the present teachings.

The first chromatography system 801 includes first and second pump systems 811 and 812, sample introducing apparatus 813, separation unit 814, detection unit 815, (optional) additional pump system 816, and processing unit 860, which may be substantially the same as discussed above. A fluid stream containing separated sample constituents or compounds is output by the separation unit 814, and peaks corresponding to the separated compounds are detected by the detection unit 815. The fluid stream containing the separated compounds (which are contained in the first dimension mobile phase continues to flow from the detection unit 815 to the transitional unit 903.

The transitional unit 903 transitions the compounds in portions of the fluid stream in which the peaks are detected from the first chromatography system 801 to the second chromatography system 802. In the depicted embodiment, the transitional unit 903 includes first valve 930, which may be an eight-port two position multi-dimension valve as shown, and second valve 940, which is a ten-port two position injection valve. Thus, the first valve 930 includes first port P11 through eighth port P18, and the second valve 940 includes first port P21 through tenth port P210. The ports may be selectively coupled or connected to one another in various configurations within and across the first and second valves 930 and 940 to enable the desired paths for the different transitional phases.

The second chromatography system 802 includes mobile phase bridge apparatus 200', separation unit 824 and detection unit 825, which may be substantially the same as discussed above. The mobile phase bridge apparatus 200' does not contain an injection unit, such as injection unit 130. Rather, the addition of sample to the combined fluid stream (eluent) from input junction 131 of the mobile phase bridge apparatus 200' occurs, as a practical matter, when the combined fluid stream passes through guard column 942, as discussed below with reference to FIG. 9C.

Referring to FIG. 9A, the first and second valves 930 and 940 are configured so that the fluid stream containing the separated compounds from the separation unit 814 and the detection unit 815 of the first chromatography system 801 flows through the first valve 930 to holding loop (or parking loop) 932 for holding compounds corresponding to peaks. In particular, the output of the detection unit 815 is connected to first port P11 of the first valve 930, which is coupled to the second port P12, which is connected to an input of the holding loop 932. An output of the holding loop 932 is connected to eighth port P18, which is coupled to fifth port P15 configured to output the fluid stream to waste. Thus, most of the sample compound relating to a peak is held in the holding loop 932, while unrelated portions of the first dimension mobile phase solution is expelled to waste.

Meanwhile, the contents of holding loop 934 are displaced, for example, using a purge gas (e.g., $CO_2$ or $N_2$) originating at fourth port P24 of the second valve 940. The fourth port P24 is coupled to fifth port P25, which is connected to seventh port P17 of the first valve 930. The seventh port P17 is coupled to sixth port P16, which is connected to an input of the holding loop 934. An output of the holding loop 934 is connected to fourth port P14, which is coupled to third port P13, which is connected to first port P21 of the second valve 940. The first port P21 is coupled to tenth port P210, which is connected to an input of the guard column 942. The displaced contents of holding loop 934 are directed to the guard column 942 where the compounds are retained due to a composition favoring partitioning onto the stationary phase of the guard column 942. In various embodiments, an additional pump system (not shown) may be utilized to selectively deliver additional weak solvent to the flow stream entering the guard column 942 to adjust the composition of the flow stream favoring retention. When included, such an additional pump system may connect to the conduit between the third valve port P13 of the first valve 930 and the first valve port P21 of the second valve 940. An output of the guard column 942 is connected to seventh port P27, which is coupled to sixth port P26 configured to output the remaining purged contents of the holding loop 934 to waste.

When the detection unit 815 and/or processing unit 860 recognizes that a peak of interest has reached the holding loop 932, the first valve 930 switches in order to move the holding loop 932 out of the first chromatography system 801 into the second chromatography system 802, as shown in FIGS. 9B and 9C.

Referring to FIG. 9B, the holding loop 932 is initially displaced by the purge gas, which displaces the first dimension mobile phase of the first chromatography system 801 from the holding loop 932 to waste (through the guard column 942 in the second chromatography system 802). The purge gas originates at the fourth port P24 of the second valve 940, which remains coupled to the fifth port P25, which is connected to seventh port P17 of the first valve 930. The seventh port P17 is coupled to the eighth port P18, which is connected to an input of the holding loop 932 for receiving the purge gas. An output of the holding loop 932 is connected to the second port P12, which is coupled to the third port P13, which is connected to the first port P21 of the second valve 940. The first port P21 remains coupled to tenth port P210, which remains connected to an input of the guard column 942. The guard column 942 retains compounds corresponding to peaks in the purged contents of the holding loop 932 (i.e., the first dimension mobile phase). An output of the guard column 942 is connected to the seventh port P27, which is coupled to sixth port P26 configured to output the remaining purged contents of the holding loop 932 to waste. Thus, most of the sample compound is retained on the guard column 942, while the first dimension mobile phase solution is expelled to waste.

Meanwhile, the fluid stream output by the detection unit 815 is directed to the holding loop 934 via the first port P11, which is coupled to the fourth port P14, which is connected to an input of the holding loop 934. An output of the holding loop 934 is connected to the sixth port P16, which is coupled to the fifth port P15 configured to output the fluid stream to waste. The holding loop 934 thus remains in the first chromatography system 801.

Referring to FIG. 9C, having previously switched the first valve 930 out of the flow stream of the first chromatography system 901, the purge gas displaces the first dimension mobile phase and "dries" the sample compounds corresponding to the detected peak now resident on the guard column 942. The second valve 940 therefore switches to pass the combined stream from the input junction 131 of the mobile phase bridge apparatus 200' into the guard column 942, in which the sample compounds from the first chromatography system 801 are retained. The retained sample compounds are eluted from the guard column 942 into the combined stream to provide a sample-containing stream, which is directed to the output junction 132 by the second valve 940. As discussed above, the combined stream may comprise a mixture of the first portion of the first mobile phase component from the first pump system 111 and the first portion of the second mobile phase component from the second pump system 112. At the output junction 132, the sample-containing stream is mixed with a second portion of the first mobile phase component (diluent) from the first pump system 111 (and possibly a second portion of the second mobile phase component of the second pump system 112) to provide the diluted sample-containing stream input to the separation unit 824 (e.g., the second dimension column). The separation unit 824 separates the compounds, which are detected by the detection unit 825 of the second chromatography system 802.

More particularly, the combined stream from the input junction 131 enters the eighth port P28 of the second valve 940, which is switched to the seventh port P27, which is connected to an input of the guard column 942. An output of the guard column 942 is connected to the tenth port P210, which is switched to couple to the ninth port P29 configured to provide the sample-containing stream to the output junction 132. The second portion of the first mobile phase component (diluent) (and any second portion of the second mobile phase component) is mixed with the sample-containing stream at the output junction 132, and the resulting diluted sample-containing stream is input to the separation unit 824, as mentioned above.

The connection configuration of the first valve 930 is unchanged, although flow is effectively reversed in order to perform a solvent wash process of the holding loop 932. The solvent wash, which may be a mixture of water and methanol, for example, cleans out the holding loop 932 removing any material not displaced by the purge gas advantageously reducing carryover between collected peaks. The solvent wash is provided to the second port P22 of the second valve 940, which is coupled to the first port P21. The first port P21 is connected to the third port P13 of the first valve 930, which remains coupled to the second port P12, which is connected to an input of the holding loop 932. An output of the holding loop 932 is connected to the eighth port P18, which remains coupled to the seventh port P17, which remains connected to the fifth port P25 of the second valve 940. The fifth port P25 is switched to the sixth port P26 configured to output the solvent wash, along with any contaminants or residue from the holding loop 932, to waste.

Meanwhile, the purge gas provided at the second port P24 is switched to plugged third port P23. Also, the fluid stream output by the detection unit 815 of the first chromatography system 801 continues to be redirected to the holding loop 934 via the first port P11 and the fourth port P14, and output from the holding loop 934 to waste via the sixth port P16 and the fifth port P15 of the first valve 930.

Once the first dimension peak has been transitioned and injected into the second dimension as shown in FIG. 9C, the second valve 940 may switch back to the configuration depicted in FIG. 9B. Accordingly, the second dimension eluent bypasses the guard column 942 being directed through the eighth port P28 coupled to the ninth port P29 of second valve 940. The guard column 942 is purged as described above in the discussion of FIG. 9B while awaiting detection of the next peak of interest when first valve 930 will again switch. With the symmetry inherent in the configuration of the first valve 930, reference to the holding loop 932 and the holding loop 934 may be used alternatively in context of flow stream participation throughout this disclosure. When the first valve 930 is in the first of its two positions, the holding loop 932 is in the first dimension flow stream and the holding loop 934 is in the control of the second valve 940 and the second dimension flow stream. When the first valve 930 is in the alternate position, the holding loop 934 is in the first dimension flow stream and the holding loop 932 is under the control of the second valve 940, as discussed above. Also, as would be apparent to one of ordinary skill in the art, multiple holding loops, arranged in parallel, may be individually addressed by multi-position selection valving (not shown) for the concomitant retention and subsequent second dimension injection of multiple first dimension sample aliquots independent of the second valve 940.

One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

What is claimed:

1. An apparatus for introducing a sample into a separation unit of a chromatography system with a mobile phase, the mobile phase comprising a first mobile phase component and a second mobile phase component, the apparatus comprising:
   an injection unit;
   a first pump system configured to provide the first mobile phase component, a first portion of the first mobile phase component flowing from the first pump system through a first branch to the injection unit, and a second portion of the first mobile phase component flowing through a second branch;
   a second pump system configured to provide the second mobile phase component, at least a first portion of the second mobile phase component flowing from the second pump system through a third branch to the injection unit; and
   an input junction configured to provide a combined stream, comprising the first portion of the first mobile phase component provided via the first branch and the first portion of the second mobile phase component provided via the third branch, wherein:
   the injection unit is configured to receive the combined stream from the input junction and to inject the sample into the combined stream to form a sample-containing stream; and
   the sample-containing stream is subsequently combined with the second portion of the first mobile phase component provided via the second branch to form a diluted sample-containing stream, which flows to the separation unit of the chromatography system for separating sample constituents.

2. The apparatus of claim 1, wherein a second portion of the second mobile phase component flows through a fourth branch.

3. The apparatus of claim 2, wherein:
the first branch comprises a first restrictor configured to restrict flow of the first mobile phase component to provide the first portion of the first mobile phase component;
the second branch comprises a second restrictor configured to restrict flow of the first mobile phase component to provide the second portion of the first mobile phase component;
the third branch comprises a third restrictor configured to restrict flow of the second mobile phase component to provide the first portion of the second mobile phase component; and
the fourth branch comprises a fourth restrictor configured to restrict flow of the second mobile phase component to provide the second portion of the second mobile phase component.

4. The apparatus of claim 3, wherein a restriction of at least one of the first through fourth restrictors is variable.

5. The apparatus of claim 3, wherein a restriction of at least one of the first through fourth restrictors is selectable, and
wherein the at least one of the first through fourth restrictors that is selectable comprises a valve for selecting one of a plurality of restrictors having different corresponding restrictions.

6. The apparatus of claim 4, wherein varying the restriction of the at least one of the first through fourth restrictors adjusts at least one of an amount of dilution of the diluted sample-containing stream and a flow rate of the combined stream.

7. The apparatus of claim 6, wherein increasing the flow of the second portion of the first mobile phase component through the second branch by varying relative restrictions of the first and second restrictors increases an amount of dilution of the diluted sample-containing stream, thereby increasing loading capacity of the separation unit of the chromatography system.

8. The apparatus of claim 1, wherein:
the first branch comprises a first restrictor configured to restrict flow of the first mobile phase component to provide the first portion of the first mobile phase component;
the second branch comprises a second restrictor configured to restrict flow of the first mobile phase component to provide the second portion of the first mobile phase component; and
the third branch comprises a third restrictor configured to restrict flow of the second mobile phase component to provide the first portion of the second mobile phase component;
wherein a restriction of at least one of the first through third restrictors is selectable, and
wherein the at least one of the first through third restrictors that is selectable comprises a valve for selecting one of a restriction or an alternative path.

9. The apparatus of claim 1, wherein respective amounts of the first portion of the first mobile phase component and the first portion of the second mobile phase component of the combined stream are selected to provide an increased flow rate of the combined stream through the injection unit.

10. The apparatus of claim 1, wherein the first mobile phase component comprises water, and the second mobile phase component comprises acetonitrile or other organic solvent.

11. The apparatus of claim 1, wherein the first mobile phase component comprises hexane or other relatively non-polar solvent, and the second mobile phase component comprises isopropanol or other relatively polar solvent.

12. The apparatus of claim 1, wherein the first mobile phase component comprises carbon dioxide, and the second mobile phase component comprises methanol or other organic solvent.

13. A method of injecting a sample in a chromatography system with a mobile phase comprising a first mobile phase component and a second mobile phase component, the method comprising:
proportioning the first mobile phase component into corresponding first and second portions of the first mobile phase component;
proportioning the second mobile phase component into corresponding first and second portions of the second mobile phase component;
combining the first portion of the first mobile phase component and the first portion of the second mobile phase component to form a combined stream;
injecting a sample solution into the combined stream to form a sample-containing stream comprising the sample solution and the first portion of the first mobile phase component and the first portion of the second mobile phase component;
after the injecting, combining the sample-containing stream with at least one of the second portion of the first mobile phase component and the second portion of the second mobile phase component to form a diluted sample-containing stream; and
passing the diluted sample-containing stream to a chromatographic column.

14. The method of claim 13, further comprising:
varying the second portion of the first mobile phase component to adjust an amount of dilution of the diluted sample-containing stream.

15. The method of claim 13, wherein:
the first portion of the first mobile phase component is between about 5 percent and about 35 percent of a first mobile phase component flow;
the first portion of the second mobile phase component is between about 65 percent and about 95 percent of a first mobile phase component flow;
the second portion of the first mobile phase component is between about 65 percent and about 95 percent of the first mobile phase component flow; and
the second portion of the second mobile phase is component between about 5 percent and about 35 percent of the second mobile phase component flow.

* * * * *